United States Patent
St. Pierre

(10) Patent No.: US 12,121,304 B2
(45) Date of Patent: Oct. 22, 2024

(54) INTRODUCER AND LOCALIZATION WIRE VISUALIZATION

(71) Applicant: Hologic, Inc., Marlborough, MA (US)

(72) Inventor: Shawn St. Pierre, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 320 days.

(21) Appl. No.: 17/031,380

(22) Filed: Sep. 24, 2020

(65) Prior Publication Data

US 2021/0000553 A1  Jan. 7, 2021

Related U.S. Application Data

(63) Continuation-in-part of application No. PCT/US2019/030615, filed on May 3, 2019.
(Continued)

(51) Int. Cl.
*A61B 34/20* (2016.01)
*A61B 8/00* (2006.01)
(Continued)

(52) U.S. Cl.
CPC ............ *A61B 34/20* (2016.02); *A61B 8/0841* (2013.01); *A61B 8/4488* (2013.01); *A61B 8/463* (2013.01);
(Continued)

(58) Field of Classification Search
CPC ... A61B 34/20; A61B 8/0841; A61B 17/3403; A61B 34/25; A61B 2017/3413; A61B 2090/3983; G01S 7/52073
See application file for complete search history.

(56) References Cited

U.S. PATENT DOCUMENTS

| 4,821,727 A | 4/1989 | Levene et al. |
| 4,907,156 A | 6/1990 | Doi et al. |
| (Continued) | | |

FOREIGN PATENT DOCUMENTS

| CN | 202161328 | 3/2012 |
| CN | 102429678 | 5/2012 |
| (Continued) | | |

OTHER PUBLICATIONS

Xia, W., West, S.J., Finlay, M.C. et al. Looking beyond the imaging plane: 3D needle tracking with a linear array ultrasound probe. Sci Rep 7, 3674 (2017). https://doi.org/10.1038/s41598-017-03886-4 (Year: 2017).*

(Continued)

*Primary Examiner* — Patrick Fernandes
*Assistant Examiner* — Nicholas A Robinson
(74) *Attorney, Agent, or Firm* — Merchant & Gould P.C.

(57) ABSTRACT

Methods and systems are disclosed for providing guidance for operation of a localization insertion device based on ultrasonic imaging. Ultrasonic waves are emitted and detected by an ultrasonic transducer to generate image data. An introducer for placing a localization wire is identified within the generated image data. Based on the identification of the introducer, the methods and systems may determine a predicted location based at least in part on introducer properties and localization wire properties. The predicted location of the ring of the localization wire may be the predicated location of the localization wire when positioned subcutaneously with the localization insertion device. At least one indicator may be displayed indicating the determined predicted ring location.

24 Claims, 19 Drawing Sheets

Related U.S. Application Data

(60) Provisional application No. 62/666,869, filed on May 4, 2018.

(51) Int. Cl.
| | | |
|---|---|---|
| *A61B 8/08* | (2006.01) | |
| *A61B 10/02* | (2006.01) | |
| *A61B 17/34* | (2006.01) | |
| *A61B 34/00* | (2016.01) | |
| *A61B 90/00* | (2016.01) | |
| *G01S 7/52* | (2006.01) | |
| *G01S 15/89* | (2006.01) | |
| *G06N 20/00* | (2019.01) | |
| *G16H 10/40* | (2018.01) | |
| *G16H 20/40* | (2018.01) | |
| *G16H 30/40* | (2018.01) | |
| *G16H 40/63* | (2018.01) | |

(52) U.S. Cl.
CPC ............ *A61B 8/485* (2013.01); *A61B 8/5215* (2013.01); *A61B 10/0275* (2013.01); *A61B 17/3403* (2013.01); *A61B 34/25* (2016.02); *A61B 90/39* (2016.02); *G01S 7/52073* (2013.01); *G01S 15/8906* (2013.01); *G06N 20/00* (2019.01); *G16H 10/40* (2018.01); *G16H 20/40* (2018.01); *G16H 30/40* (2018.01); *G16H 40/63* (2018.01); *A61B 8/0825* (2013.01); *A61B 8/481* (2013.01); *A61B 2017/3413* (2013.01); *A61B 2034/2063* (2016.02); *A61B 2034/2065* (2016.02); *A61B 2090/378* (2016.02); *A61B 2090/3925* (2016.02); *A61B 2090/3983* (2016.02)

(56) References Cited

U.S. PATENT DOCUMENTS

| | | |
|---|---|---|
| 5,078,142 A | 1/1992 | Siczek et al. |
| 5,129,911 A | 7/1992 | Siczek et al. |
| 5,133,020 A | 7/1992 | Giger et al. |
| 5,219,351 A | 6/1993 | Teubner |
| 5,240,011 A | 8/1993 | Assa |
| 5,280,427 A | 1/1994 | Magnusson |
| 5,289,520 A | 2/1994 | Pellegrino et al. |
| 5,343,390 A | 8/1994 | Doi et al. |
| 5,386,447 A | 1/1995 | Siczek |
| 5,415,169 A | 5/1995 | Siczek et al. |
| 5,426,685 A | 6/1995 | Pellegrino et al. |
| 5,491,627 A | 2/1996 | Zhang et al. |
| 5,594,769 A | 1/1997 | Pellegrino et al. |
| 5,609,152 A | 3/1997 | Pellegrino et al. |
| 5,735,264 A | 4/1998 | Siczek et al. |
| 5,769,086 A | 6/1998 | Ritchart et al. |
| 5,773,832 A | 6/1998 | Sayed et al. |
| 5,803,912 A | 9/1998 | Siczek et al. |
| 6,022,325 A | 2/2000 | Siczek et al. |
| 6,101,236 A | 8/2000 | Wang et al. |
| 6,102,866 A | 8/2000 | Nields et al. |
| 6,245,028 B1 | 6/2001 | Furst et al. |
| 6,293,282 B1 | 9/2001 | Lemelson |
| 6,459,925 B1 | 10/2002 | Nields et al. |
| 6,468,226 B1 | 10/2002 | McIntyre, IV |
| 6,480,565 B1 | 11/2002 | Ning |
| 6,620,111 B2 | 9/2003 | Stephens et al. |
| 6,626,849 B2 | 9/2003 | Huitema et al. |
| 6,638,235 B2 | 10/2003 | Miller et al. |
| 6,683,934 B1 | 1/2004 | Zhao |
| 6,733,458 B1 * | 5/2004 | Steins ................ A61B 8/4254 600/461 |
| 6,758,824 B1 | 7/2004 | Miller et al. |
| 6,987,331 B2 | 1/2006 | Koeppe |
| 7,123,684 B2 | 10/2006 | Jing et al. |
| 7,245,694 B2 | 7/2007 | Jing et al. |
| 7,466,795 B2 | 12/2008 | Eberhard et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,697,660 B2 | 4/2010 | Ning |
| 7,702,142 B2 | 4/2010 | Ren et al. |
| 7,760,924 B2 | 7/2010 | Ruth et al. |
| 7,787,936 B2 | 8/2010 | Kressy |
| 7,831,296 B2 | 11/2010 | DeFreitas et al. |
| 7,869,563 B2 | 1/2011 | DeFreitas |
| 7,991,106 B2 | 8/2011 | Ren et al. |
| 8,532,745 B2 | 9/2013 | DeFreitas et al. |
| 8,594,274 B2 | 11/2013 | Hoernig et al. |
| 9,020,579 B2 | 4/2015 | Smith |
| 9,901,309 B2 | 2/2018 | DeFreitas et al. |
| 10,092,358 B2 | 10/2018 | DeFreitas |
| 10,335,094 B2 | 7/2019 | DeFreitas |
| 10,357,211 B2 | 7/2019 | Smith |
| 10,456,213 B2 | 10/2019 | DeFreitas |
| 10,595,954 B2 | 3/2020 | DeFreitas |
| 2001/0038681 A1 | 11/2001 | Stanton et al. |
| 2002/0113681 A1 | 8/2002 | Byram |
| 2003/0018272 A1 | 1/2003 | Treado et al. |
| 2003/0073895 A1 | 4/2003 | Nields et al. |
| 2003/0135115 A1 | 7/2003 | Burdette et al. |
| 2004/0077938 A1 | 4/2004 | Mark et al. |
| 2004/0081273 A1 | 4/2004 | Ning |
| 2004/0127789 A1 | 7/2004 | Ogawa |
| 2004/0171933 A1 | 9/2004 | Stoller et al. |
| 2004/0171986 A1 | 9/2004 | Tremaglio, Jr. et al. |
| 2004/0267157 A1 | 12/2004 | Miller et al. |
| 2005/0049521 A1 | 3/2005 | Miller et al. |
| 2005/0084060 A1 | 4/2005 | Seppi et al. |
| 2005/0089205 A1 | 4/2005 | Kapur |
| 2005/0111718 A1 | 5/2005 | MacMahon |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |
| 2006/0009693 A1 | 1/2006 | Hanover et al. |
| 2006/0025680 A1 | 2/2006 | Jeune-Iomme |
| 2006/0030784 A1 | 2/2006 | Miller et al. |
| 2006/0098855 A1 | 5/2006 | Gkanatsios et al. |
| 2006/0129062 A1 | 6/2006 | Nicoson et al. |
| 2006/0155209 A1 | 6/2006 | Miller et al. |
| 2006/0149194 A1 * | 7/2006 | Conston ............... A61F 9/00763 604/294 |
| 2006/0257009 A1 | 11/2006 | Wang |
| 2006/0269040 A1 | 11/2006 | Mertelmeier |
| 2007/0016067 A1 * | 1/2007 | Webster, III ........... A61B 90/10 600/464 |
| 2007/0019846 A1 | 1/2007 | Bullitt et al. |
| 2007/0114424 A1 | 5/2007 | Danielsson et al. |
| 2007/0167822 A1 * | 7/2007 | Webler ................... A61B 90/36 600/463 |
| 2007/0225600 A1 | 9/2007 | Weibrecht et al. |
| 2007/0263765 A1 | 11/2007 | Wu |
| 2008/0019581 A1 | 1/2008 | Gkanatsios et al. |
| 2008/0045833 A1 | 2/2008 | DeFreitas et al. |
| 2008/0101537 A1 | 5/2008 | Sendai |
| 2008/0152086 A1 | 6/2008 | Hall |
| 2008/0187095 A1 | 8/2008 | Boone et al. |
| 2008/0198966 A1 | 8/2008 | Hjarn |
| 2009/0003519 A1 | 1/2009 | DeFreitas |
| 2009/0080604 A1 | 3/2009 | Shores et al. |
| 2009/0143674 A1 | 6/2009 | Nields |
| 2009/0171244 A1 | 7/2009 | Ning |
| 2009/0296882 A1 | 12/2009 | Gkanatsios et al. |
| 2010/0034348 A1 | 2/2010 | Yu |
| 2010/0098214 A1 | 4/2010 | Star-Lack et al. |
| 2010/0135558 A1 | 6/2010 | Ruth et al. |
| 2010/0152570 A1 | 6/2010 | Navab |
| 2010/0208037 A1 | 8/2010 | Sendai |
| 2010/0305439 A1 * | 12/2010 | Shai ...................... A61B 18/02 434/262 |
| 2011/0019891 A1 | 1/2011 | Puong |
| 2011/0069808 A1 | 3/2011 | Defreitas et al. |
| 2011/0087132 A1 | 4/2011 | DeFreitas et al. |
| 2011/0110576 A1 | 5/2011 | Kreeger |
| 2011/0112549 A1 | 5/2011 | Neubach |

(56) References Cited

U.S. PATENT DOCUMENTS

| | | |
|---|---|---|
| 2011/0182402 A1 | 7/2011 | Partain |
| 2011/0237927 A1 | 9/2011 | Brooks et al. |
| 2011/0237947 A1 | 9/2011 | Boctor |
| 2011/0245659 A1 | 10/2011 | Ma |
| 2011/0313288 A1 | 12/2011 | Chi Sing |
| 2012/0014504 A1 | 1/2012 | Jang |
| 2012/0134464 A1 | 5/2012 | Hoernig et al. |
| 2012/0172722 A1* | 7/2012 | Chinowsky ........ A61B 17/3403 600/443 |
| 2012/0238870 A1 | 9/2012 | Smith et al. |
| 2012/0239087 A1* | 9/2012 | Field ...................... A61B 90/39 606/232 |
| 2013/0022165 A1 | 1/2013 | Jang |
| 2013/0044861 A1 | 2/2013 | Muller |
| 2013/0108138 A1 | 5/2013 | Nakayama |
| 2013/0259193 A1 | 10/2013 | Packard |
| 2014/0064444 A1 | 3/2014 | Oh |
| 2014/0073913 A1 | 3/2014 | DeFreitas et al. |
| 2014/0094695 A1 | 4/2014 | Jain |
| 2016/0000399 A1 | 1/2016 | Halmann et al. |
| 2016/0022364 A1 | 1/2016 | DeFreitas et al. |
| 2016/0235380 A1 | 8/2016 | Smith |
| 2016/0324501 A1* | 11/2016 | Vignon ............... A61B 8/0841 |
| 2017/0340352 A1 | 11/2017 | Stone et al. |
| 2018/0000446 A1 | 1/2018 | Lu |
| 2018/0132927 A1* | 5/2018 | Chen ...................... A61B 90/37 |
| 2018/0132944 A1* | 5/2018 | Yan ............................ G06T 7/74 |
| 2018/0256118 A1 | 9/2018 | DeFreitas |
| 2019/0008605 A1* | 1/2019 | Matsushima ............ A61B 6/12 |
| 2019/0015173 A1 | 1/2019 | DeFreitas |
| 2019/0105017 A1* | 4/2019 | Hastings .............. A61B 8/4444 |
| 2019/0110924 A1* | 4/2019 | Moreno ............. A61B 17/3415 |
| 2019/0290221 A1 | 9/2019 | Smith |
| 2020/0000442 A1 | 1/2020 | Vancamberg |
| 2020/0046303 A1 | 2/2020 | DeFreitas |
| 2020/0093562 A1 | 3/2020 | DeFreitas |
| 2020/0205928 A1 | 7/2020 | DeFreitas |
| 2020/0281662 A1* | 9/2020 | Cong ...................... A61B 34/10 |
| 2020/0390404 A1 | 12/2020 | DeFreitas |
| 2021/0100626 A1 | 4/2021 | St. Pierre |

FOREIGN PATENT DOCUMENTS

| | | |
|---|---|---|
| CN | 106687049 | 5/2017 |
| CN | 107106126 A | 8/2017 |
| CN | 107666876 A | 2/2018 |
| DE | 102011087127 | 5/2013 |
| EP | 2236085 | 6/2010 |
| EP | 2491863 | 8/2012 |
| EP | 1986548 | 1/2013 |
| EP | 2656789 | 10/2013 |
| EP | 3060132 | 4/2019 |
| JP | 2000-107178 | 4/2000 |
| JP | 2003-531516 | 10/2003 |
| JP | 2006-519634 | 8/2006 |
| JP | 2007-130487 | 5/2007 |
| JP | 2009-522005 | 6/2009 |
| JP | 2009-526618 | 7/2009 |
| JP | 2010-137004 | 6/2010 |
| JP | 2012/501750 | 1/2012 |
| JP | 2014-507250 | 3/2014 |
| JP | 2015-506794 | 3/2015 |
| WO | 93/17620 | 9/1993 |
| WO | 94/06352 | 3/1994 |
| WO | 1997/00649 | 1/1997 |
| WO | 00/51484 | 9/2000 |
| WO | 2005/110230 | 11/2005 |
| WO | 2005/112767 | 12/2005 |
| WO | 2006/055830 | 5/2006 |
| WO | 2006/058160 | 6/2006 |
| WO | 08/014670 | 2/2008 |
| WO | 2008/054436 | 5/2008 |
| WO | 2010/028208 | 3/2010 |
| WO | 2012/068373 | 5/2012 |
| WO | 2012/112627 | 8/2012 |
| WO | 2012/122399 | 9/2012 |
| WO | 2013/078476 | 5/2013 |
| WO | 2013/123091 | 8/2013 |
| WO | 2015/061582 | 4/2015 |
| WO | 2016/103094 | 6/2016 |
| WO | 2016/184746 | 11/2016 |
| WO | 2019/213532 | 11/2019 |

OTHER PUBLICATIONS

J. Carriere, C. Rossa, R. Sloboda, N. Usmani and M. Tavakoli, "Real-time needle shape prediction in soft-tissue based on image segmentation and particle filtering," 2016 IEEE International Conference on Advanced Intelligent Mechatronics (AIM), Banff, AB, Canada, 2016 (Year: 2016).*

"Filtered Back Projection", (NYGREN), published May 8, 2007, URL: http://web.archive.org/web/19991010131715/http://www.owlnet.rice.edu/~elec539/Projects97/cult/node2.html, 2 pgs.

Berg WA et al., "Combined screening with ultrasound and mammography vs mammography alone in women at elevated risk of breast cancer", JAMA 299:2151-2163, 2008.

Canadian Office Action in Application 2829349, mailed Oct. 15, 2018, 4 pages.

Carton AK, et al., "Dual-energy contrast-enhanced digital breast tomosynthesis—a feasibility study", BR J Radiol. Apr. 2010;83 (988):344-50.

Chen SC, et al., "Initial clinical experience with contrast-enhanced digital breast tomosynthesis", Acad Radio. Feb. 2007 14(2):229-38.

Chinese 2nd Office Action in Application 201480058064.5, mailed Jul. 16, 2019, 5 pgs.

Diekmann F., et al., "Digital mammography using iodine-based contrast media: initial clinical experience with dynamic contrast medium enhancement", Invest Radiol 2005; 40:397-404.

Dromain C., et al., "Contrast enhanced spectral mammography: a multi-reader study", RSNA 2010, 96th Scientific Assembly and Scientific Meeting.

Dromain C., et al., "Contrast-enhanced digital mammography", Eur J Radiol. 2009; 69:34-42.

European Communication in Application 10707751.3, mailed Oct. 4, 2018, 5 pages. (corresponding to matter).

European Communication in Application 10707751.3, mailed Aug. 7, 2019, 6 pages.

European Extended Search Report dated Jul. 18, 2014 in EP App 12754521.8, 7 pages.

European Extended Search Report for European Patent Application No. 14770362.3 mailed Sep. 28, 2016, 8 pgs.

European Extended Search Report in Application 14855181.5, mailed May 15, 2017, 7 pages.

European extended Search Report in Application 18153706.9, mailed Jun. 1, 2018, 8 pages.

European Mar. 23, 2009 European Search Report in connection with counterpart European patent Application No. 07750818.

European Office Action in Application 10707751.3, mailed Feb. 19, 2018, 5 pgs.

Freiherr G., "Breast tomosynthesis trials show promise", Diagnostic Imaging—San Francisco 2005, V27; N4:42-48.

Giger, M. et al., "An "Intelligent" Workstation for Computer-aided Diagnosis", RadioGraphics, (1993), 13(3): 647-656.

Giger, M. et al., "Development of a "smart" workstation for use in mammography", Proceedings of SPIE, (1991), 45: 101-103.

Hologic, "Lorad StereoLoc II" Operator's Manual 9-500-0261, Rev. 005, 2004, 78 pgs.

Hologic, Inc., 510(k) Summary, prepared Nov. 28, 2010, for Affirm Breast Biopsy Guidance System Special 510(k) Premarket Notification, 5 pages.

Hologic, Inc., 510(k) Summary, prepared Aug. 14, 2012, for Affirm Breast Biopsy Guidance System Special 510(k) Premarket Notification, 5 pages.

ICRP Publication 60: 1990 Recommendations of the International Commission on Radiological Protection, 12 pages.

(56) References Cited

OTHER PUBLICATIONS

Japanese Notice of Final Rejection in Application 2016-526115, mailed Jun. 24, 2019, 5 pages.
Jochelson M., et al, "Bilateral Dual Energy contrast-enhanced digital mammography: Initial Experience", RSNA 2010, 96th Scientific Assembly and Scientific Meeting, 1 page.
Jong, RA, et al., Contrast-enhanced digital mammography: initial clinical experience. Radiology 2003; 228:842-850.
Kopans, et.al. Will tomosynthesis replace conventional mammography? Plenary Session SFN08: RSNA 2005.
Lehman CD, et al. MRI evaluation of the contralateral breast in women with recently diagnosed breast cancer. N Engl J Med 2007; 356:1295-1303.
Lewin JM, et al., Dual-energy contrast-enhanced digital subtraction mammography: feasibility. Radiology 2003; 229:261-268.
Lindfors KK, et al., Dedicated breast CT: initial clinical experience. Radiology 2008; 246(3): 725-733.
Niklason, L., et al., Digital tomosynthesis in breast imaging. Radiology. Nov. 1997; 205(2):399-406.
Observations by Third Party, Remarks concerning European patent application No. 10707751.3 according to Article 115 EPC, dated Apr. 24, 2014, 8 pgs.
PCT Feb. 20, 2008 International Search Report and Written Opinion in connection with corresponding International patent application No. PCT/US2007/04006, 7 pgs.
PCT International Preliminary Report on Patentability in International Application PCT/US2014/061994, mailed Apr. 26, 2016, 5 pages.
PCT International Search Report and Written Opinion in Application PCT/US2010/025873, dated Aug. 2, 2010, 19 pgs.
PCT International Search Report in Application PCT/US2014/026164, mailed Jul. 28, 2014, 1 page.
PCT International Search Report for International Application PCT/US2014/026164, mailed Jul. 28, 2014, 2 pgs.
PCT Written Opinion in International Application PCT/US2014/061994, mailed Jan. 22, 2015, 4 pages.
PCT/US12/28334 International Search Report and Written Opinion, dated Jul. 5, 2012, 7 pages.
Poplack SP, et al., Digital breast tomosynthesis: initial experience in 98 women with abnormal digital screening mammography. AJR Am J Roentgenology Sep. 2007 189(3):616-23.
Prionas ND, et al., Contrast-enhanced dedicated breast CT: initial clinical experience. Radiology. Sep. 2010 256(3):714-723.
Rafferty E. et al., "Assessing Radiologist Performance Using Combined Full-Field Digital Mammography and Breast Tomosynthesis Versus Full-Field Digital Mammography Alone: Results". . . presented at 2007 Radiological Society of North America meeting, Chicago IL.
Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.
Smith, A., Full field breast tomosynthesis. Radiol Manage. Sep.-Oct. 2005; 27(5):25-31.
Weidner N, Semple JP, Welch WR, Folkman J. Tumor angiogenesis and metastasis: correlation in invasive breast carcinoma. New England Journal of Medicine 1991; 324:1-8.
Weidner N, The importance of tumor angiogenesis: the evidence continues to grow. AM J Clin Pathol. Nov. 2004 122(5):696-703.
PCT International Search Report and Written Opinion in Application PCT/US2019/030615, mailed Sep. 17, 2019, 13 pages.
"Supersonic to feature Aixplorer Ultimate at ECR", AuntiMinnie.com, 3 pages (Feb. 2018).
European Extended Search Report in Application 21198835.7, mailed Feb. 17, 2022, 8 pages.
Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.
Dromain, Clarisse et al., "Dual-energy contrast-enhanced digital mammography: initial clinical results", European Radiology, Sep. 14, 2010, vol. 21, pp. 565-574.
Reynolds, April, "Stereotactic Breast Biopsy: A Review", Radiologic Technology, vol. 80, No. 5, Jun. 1, 2009, pp. 447M-464M, XP055790574.
"SuperSonic to feature Aixplorer Ultimate at ECR"; obtained online on Dec. 21, 2023 at: https://www.auntminnie.com/clinical-news/ultrasound/article/15619739/supersonic-to-feature-aixplorer-ultimate-at-ecr, published Feb. 25, 2018, 3 pages.
"SuperSonic Imagine holds 30 international patent families protecting its unique ultrasound imaging technology around the world", obtained online on Dec. 21, 2023 at: https://www.supersonicimagine.com/Aixplorer-MACH2/TECHNOLOGY, 1 page.

* cited by examiner

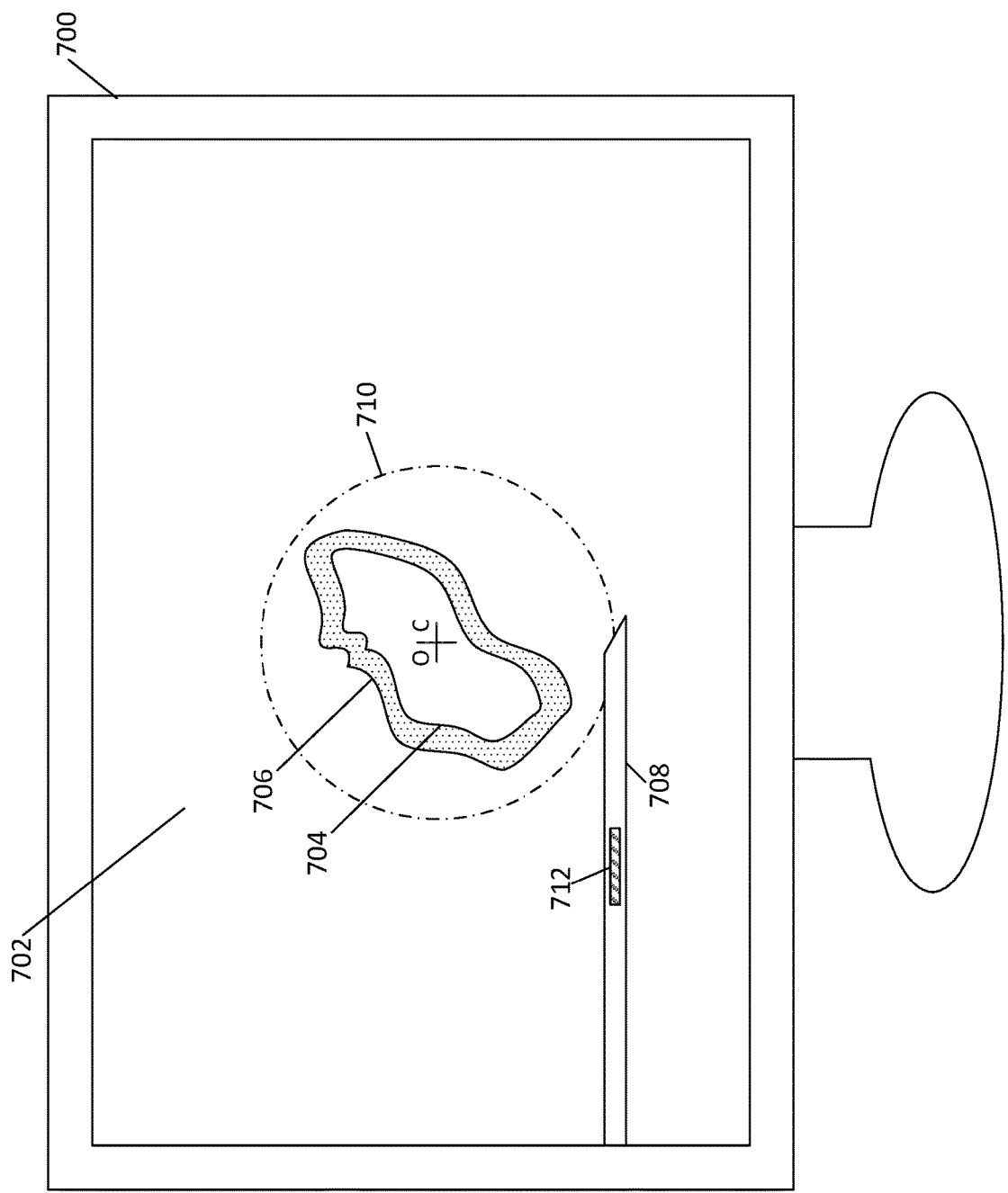

INTRODUCER AND LOCALIZATION WIRE VISUALIZATION

CROSS-REFERENCE TO RELATED APPLICATIONS

This application is a continuation-in-part of PCT International Patent Application No. PCT/US2019/030615, filed May 3, 2019, titled "Biopsy Needle Visualization," which claims priority to and the benefit of U.S. Provisional Patent Application Ser. No. 62/666,869, filed May 4, 2018, titled "Biopsy Needle Visualization," the disclosures of which are hereby incorporated by reference herein in their entireties.

BACKGROUND

A biopsy is a procedure that is used to extract tissue from a targeted location of a patient for further examination. For example, a lesion or mass may be identified within the patient, and a sample of that lesion or mass is desired for further testing, analysis, or examination. During some biopsy procedures, such as a percutaneous core biopsy, a surgeon or medical professional inserts a biopsy needle into the patient through an incision of the skin of the patient. To target and/or visualize the lesion accurately with the biopsy needle, various imaging modalities are employed, including the use of ultrasound technology to view an image of the needle in a subcutaneous position. While such use of ultrasound technology is useful, prior ultrasound guided biopsy technology provides visual indication but limited additional information about the lesion or of the biopsy needle and provides little guidance or insights to the medical professional performing the biopsy procedure. The biopsy procedure thus relied heavily on the skill, experience, and intuition of the medical professional.

A lumpectomy is a procedure that may be used to remove an identified lesion or mass identified within the patient. For example, a lesion or mass may be identified for extraction after analysis of a biopsy of the lesion or mass. During some lumpectomy procedures, a localization wire or localization seed may be placed in the patient prior to surgery to assist in surgical guidance and verification of lesion or mass removal. Accurate placement of such localization wire or seeds also has traditionally relied heavily on the skill, experience, and intuition of the medical professional.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for the localization of an implanted marker through ultrasound technology along with additional combinations of other modalities.

In an aspect, the technology relates to a method for providing guidance for an introducer. The method includes emitting an array of ultrasonic sound waves from an ultrasonic transducer of an ultrasound probe and detecting reflected ultrasonic sound waves by the ultrasonic transducer, wherein the reflected ultrasonic sound waves include at least a portion of the array of ultrasonic sound waves after being reflected from an interior of a patient. The method further includes generating image data from the reflected ultrasonic sound waves. Additionally, the method includes identifying, by a processor, within the generated image data, at least a portion of an introducer within the interior of the patient. Based at least in part on the identification of the introducer, the method includes determining, by the processor, a predicted location of a ring of a localization wire capable of being placed by the introducer by advancing the localization wire out of the introducer. The method further includes displaying, on a display operatively connected to the processor, an ultrasound image based on the generated image data; and displaying, on the ultrasound image, at least one indicator for the predicted location of the ring.

In an example, the ring is a portion of the localization wire having shape memory characteristics. In another example, displaying the at least one indicator for the predicted location of the ring includes displaying at least one of an in-plane predicted ring center of the ring or a predicted ring location of the ring. In a further example, identifying the introducer comprises determining an orientation of the introducer based on an orientation marker on the introducer, and wherein an orientation of the ring is based on the orientation of the introducer. In yet another example, the method further includes determining a deflection probability for the predicted location of the ring based on at least one of: (1) experimental data for the type of ring and (2) one or more stored properties of the ring, the properties including at least one of a ring diameter, a gauge of the ring, a ring material composition, a ring tip geometry, and a ring extension property. In still a further example, the one or more stored properties of the ring are based on user input regarding a size of the ring.

In an example, determining the deflection probability is further based on tissue properties of the interior of the patient along a ring trajectory for the ring. In another example, the method further includes displaying a deflection probability indicator on the ultrasound image, wherein the deflection probability indicator indicates a range for a ring location based on the determined deflection probability. In a further example, the deflection probability indicator indicates a range of probabilities for the predicted ring location. In yet another example, the method further includes: determining that a portion of the predicted ring location is outside of an imaging plane of the ultrasound image; and in response to determining that the portion of the predicted ring location is outside of the imaging plane, displaying an orientation alert. In still a further example, the orientation alert includes displaying a recommended correction angle to rotate the introducer.

In an example, the method further includes determining that the introducer is not in a deployment position; and in response to determining that the introducer is not in the deployment position, displaying a position alert. In another example, determining that the introducer is not in the deployment position includes one of: comparing an in-plane predicted ring center with a lesion center; or comparing the predicted location of the ring with a boundary of a lesion. In a further example, the position alert includes displaying a recommended correction distance to move the introducer. In yet another example, the method further includes determining that the introducer has diverted out of the imaging plane for the ultrasound image, including: determining a first apparent depth for the introducer at a first time; determining a second apparent depth for the introducer at a second time subsequent to the first time, the second apparent depth being greater than the first apparent depth; determining a third apparent depth for the introducer at a third time subsequent to the second time, the third apparent depth being less than the second apparent depth; and based on the third apparent depth being less than the second apparent depth and the second apparent depth being greater than the first apparent depth, determining that the introducer has diverted out of the imaging plane for the ultrasound image.

In another aspect, a system is disclosed. The system includes an ultrasound probe comprising an ultrasonic transducer, the ultrasonic transducer configured to emit an array of ultrasonic sound waves and detect reflected ultrasonic sound waves, wherein the reflected ultrasonic sound waves include at least a portion of the array of ultrasonic sound waves after being reflected within an interior of a patient. The system further includes a display. Additionally, the system includes at least one processor operatively connected to the display and the ultrasound probe, and memory, operatively connected to the at least one processor, storing instructions that when executed by the at least one processor perform a set of operations. The set of operations include generating image data from the reflected ultrasonic sound waves and identifying, by the at least one processor, within the generated image data, a introducer within the interior of the patient. Based at least in part on the identification of the introducer, the set of operations includes determining, by the at least one processor, a predicted location of a ring capable of being placed by the introducer at least in part on one or more ring introducer properties stored the memory. The set of operations further includes displaying, on a display operatively connected to the processor, an ultrasound image based on the generated image data. Additionally, the set of operations includes displaying, on the ultrasound image, at least one indicator for the predicted location of the ring.

In another aspect, a method for providing guidance for placement of a localization wire with an introducer is disclosed. The method includes displaying a user interface for selecting a ring to be used for a localization procedure, wherein the ring is a portion of a localization wire capable of being placed by an introducer. Additionally, the method includes receiving a selection of the ring at the user interface, the selected ring to be used for the localization procedure. The method further includes determining ring properties for the selected ring, wherein the ring properties include at least one of a ring diameter, a ring gauge, a ring material composition, a ring tip geometry, or a ring extension property. The method includes emitting an array of ultrasonic sound waves from an ultrasonic transducer of an ultrasound probe, and detecting reflected ultrasonic sound waves by the ultrasonic transducer, wherein the reflected ultrasonic sound waves include at least a portion of the array of ultrasonic sound waves after being reflected from an interior of a patient. The method further includes generating an ultrasound image from the reflected ultrasonic sound waves. Additionally, the method includes identifying the introducer within the generated ultrasound image, and determining a position and an orientation of the introducer. Based on the position and orientation of the introducer and the determined ring properties, the method includes determining a predicted ring location of the selected ring. Based on the predicted ring location, the method includes displaying the predicted ring location indicator.

In an example, the method further includes displaying a position notification and orientation notification for the introducer, wherein the position notification includes displaying a recommended correction distance in a direction to move the introducer and wherein the orientation notification includes displaying a recommended correction angle to rotate the introducer. In another example, the method further includes, based on the position and orientation of the introducer and the determined ring properties, estimating a predicted ring center of the selected ring; identifying a lesion within the generated ultrasound image, the lesion having a boundary and a center; and determining that the introducer is in a deployment position based on one or more of: the predicted ring location and the boundary of the lesion; or the predicted ring center and the center of the lesion. In a further example, determining the orientation of the introducer includes identifying an orientation marker associated with the introducer within the generated ultrasound image.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

FIGS. 7D-E depict example ultrasound images including the lesion of FIG. 7A, an introducer, and a predicted ring location of a localization wire, where the introducer and the lesion are both in the imaging plane of the ultrasound image.

DETAILED DESCRIPTION

Figure 1A:
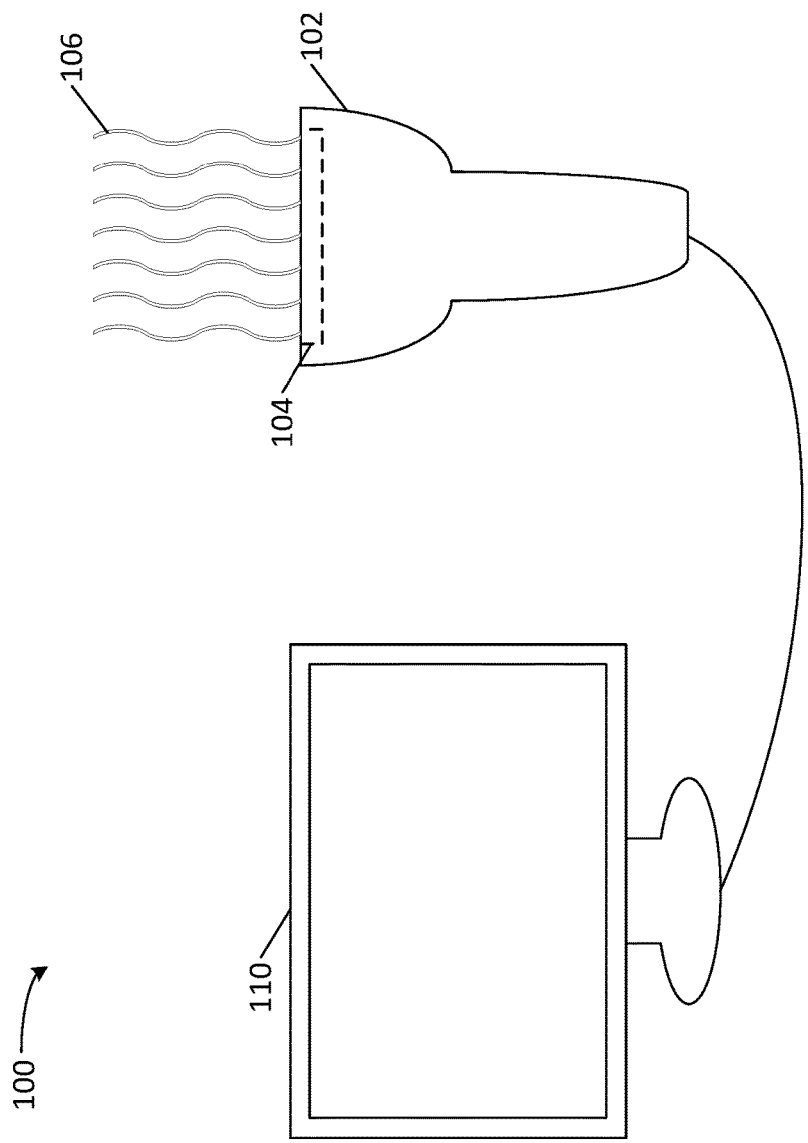
FIG. 1A depicts an example of a biopsy needle visualization system.

Proper positioning of a biopsy needle is important for a successful biopsy procedure. In situations where the biopsy needle is not properly positioned, a biopsy procedure may need to be performed repeatedly until a desired sample is obtained. Incorrect positioning can also lead to repeated steps during the procedure, additional sample being acquired during the same procedure, and/or a patient having to return for additional follow-up biopsy procedures. Proper positioning of a biopsy needle, however, becomes more difficult with the use of different biopsy needles. As an example, some biopsy needles are spring-loaded and have other "firing" mechanisms that cause a portion of the biopsy needle to extend to capture a sample. For instance, an outer cannula of a biopsy needle may be inserted into the patient, and upon a release mechanism being triggered, an inner cannula with an aperture is fired from within the outer cannula such that the inner cannula extends further into the patient to capture a sample. Examples of such biopsy needles include the Celero® biopsy device and the Sertera® biopsy device from Hologic, Inc., of Marlborough, Massachusetts. Even with ultrasound images of such biopsy needles in their subcutaneous position, the post-fire positions of the biopsy needle are still unknown. That is, while a portion of a biopsy needle in its pre-fire configuration may be seen on an ultrasound image, the final location of the biopsy needle in its post-fire configuration is not necessarily discernable from an ultrasound image alone.

Many biopsy procedures, even those with prior ultrasound technology, relied heavily on the skill, experience, and intuition of the medical professional performing the biopsy procedure. While some well-trained and experienced medical professionals are able to approximate where the biopsy needle might be located in its post-fire position, less experienced medical professionals may have trouble making such approximations. Further, the biopsy needles vary between different brands and models, adding further unpredictability to the process. For instance, one biopsy needle may deflect more than another when fired, and such deflection may also depend on the particular tissue for which the biopsy needle will pass through when fired. These deflections are extremely difficult, if not impossible, for even experienced surgeons to predict. In addition, there is variability in the nature and composition of the patient's breast tissue, can cause some unpredictability in the final location of the biopsy needle, post-fire.

To alleviate those problems, among others, the present technology provides for a biopsy needle visualization system that provides more precise and useful feedback during the biopsy procedure to allow a medical professional to more accurately position the biopsy needle. As example, the biopsy needle visualization system may provide indicia for a predicted location and/or position of the biopsy needle in its post-fire configuration based on its pre-fire configuration. The predicted location of the biopsy needle may be displayed as an overlay preferably on a live, or real-time, ultrasound image of the biopsy needle and the targeted location for the biopsy needle. Thus, the medical professional is provided with additional guidance to perform a more accurate sampling of tissue using the biopsy needle. For instance, if the surgeon sees that the predicted location is not the targeted location, the medical professional is able to adjust the biopsy needle to the proper position. The predicted location of the biopsy needle may be displayed as a set of biopsy prediction indicators that may indicate the predicted location of the tip of the biopsy needle and the aperture of the biopsy needle. The predictions also may be based on the properties of the biopsy needle that is currently being used to perform the biopsy. Accordingly, the guidance provided to the surgeon is specific to the specific biopsy needle in use, allowing for the medical professional to perform the biopsy even if he or she has never used that particular needle before. The composition of the patient's breast tissue which may be determined or indicated by the medical professional during the procedure may also be used to determine the predicted location of the biopsy needle, providing for an even more accurate prediction. Thus, the technologies described herein provide improved performance for both well-experienced and less-experienced surgeons.

FIG. 1A depicts an example of a biopsy needle visualization system 100. The biopsy needle visualization system 100 includes an ultrasound probe 102 that includes an ultrasonic transducer 104. The ultrasonic transducer 104 is configured to emit an array of ultrasonic sound waves 106. The ultrasonic transducer 104 converts an electrical signal into ultrasonic sound waves 106. The ultrasonic transducer 104 may also be configured to detect ultrasonic sound waves, such as ultrasonic sound waves that have been reflected from internal portions of a patient. In some examples, the ultrasonic transducer 104 may incorporate a capacitive transducer and/or a piezoelectric transducer, as well as other suitable transducing technology.

The ultrasonic transducer 104 is also operatively connected (e.g., wired or wirelessly) to a display 110. The display 110 may be a part of a computing system, including processors and memory configured to produce and analyze ultrasound images. Further discussion of a suitable computing system is provided below with reference to FIG. 1G. The display 110 is configured to display ultrasound images based on an ultrasound imaging of a patient. The ultrasound imaging performed in the biopsy needle visualization system 100 is primarily B-mode imaging, which results in a two-dimensional ultrasound image of a cross-section of a portion of the interior of a patient. The brightness of the pixels in the resultant image generally corresponds to amplitude or strength of the reflected ultrasound waves. Other ultrasound imaging modes may also be utilized. While the term transceiver is used herein, the term is intended to cover both transmitters, receivers, and transceivers, along with any combination thereof.

Figure 1B:
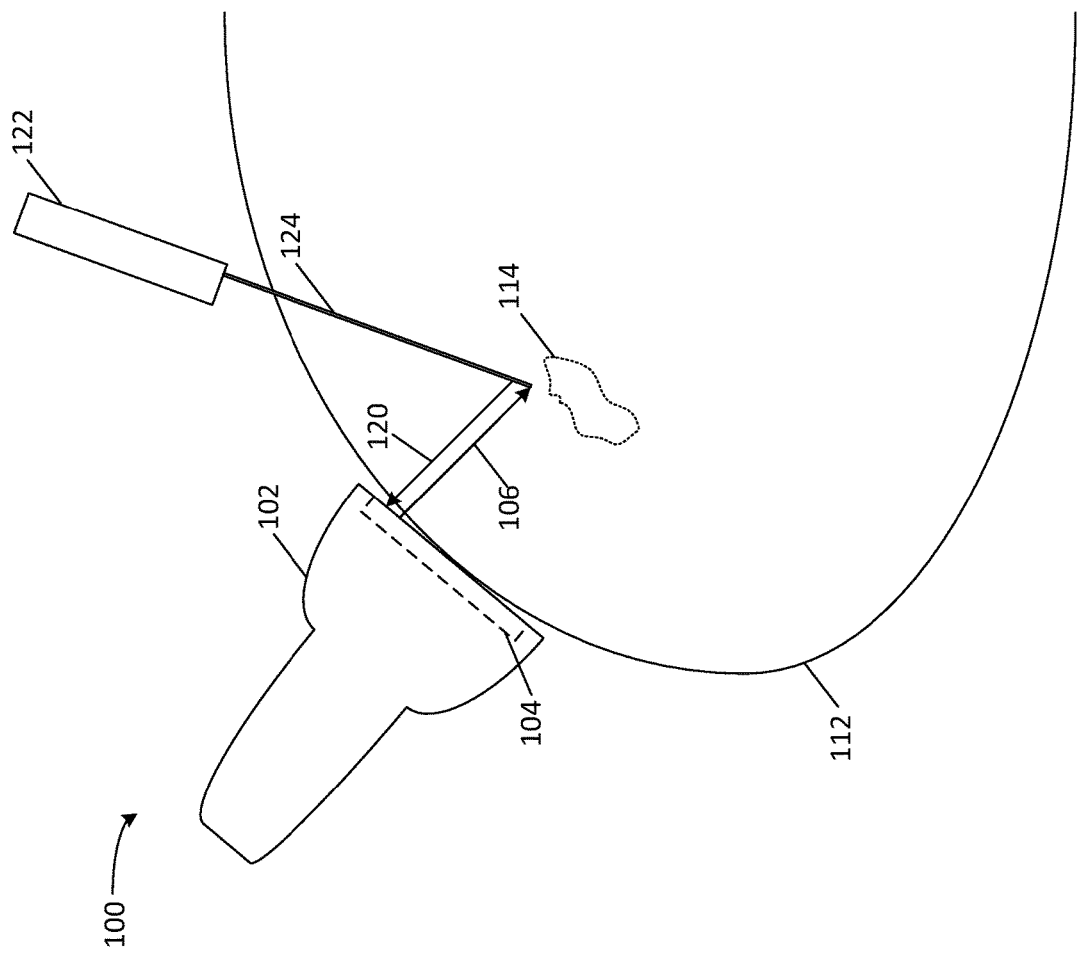
FIG. 1B depicts an example of the biopsy needle visualization system with a biopsy needle in a pre-fire configuration.

FIG. 1B depicts an example of the biopsy needle visualization system 100 with a biopsy needle 124 in a pre-fire configuration. The ultrasound probe 102 is in contact with a portion of the patient 112, such as a breast of the patient 112. In the position depicted in FIG. 1B, the ultrasound probe 102 is being used to image a portion of the patient 112 containing a lesion 114. A biopsy device 122 having a biopsy needle 124 is inserted into the patient 112. The biopsy needle 124 is depicted in its pre-fire configuration. To image the portion of the patient 112 containing the biopsy needle 124, the ultrasonic transducer 104 emits an array of ultrasonic sound waves 106 into the interior of the patient 112. A portion of the ultrasonic sound waves 106 are reflected off internal features of the patient 112 as well as the biopsy needle 124, when the biopsy needle 124 is in the field of view, and return to the ultrasound probe 102 as reflected ultrasonic sound waves 120. The reflected ultrasonic sound waves 120 may be detected by the ultrasonic transducer 104. For instance, the ultrasonic transducer 104 receives the reflected ultrasonic sound waves 120 and converts the ultrasonic sound waves 120 into an electric signal that can be processed and analyzed to generate ultrasound image data on display 110.

Figure 1C:
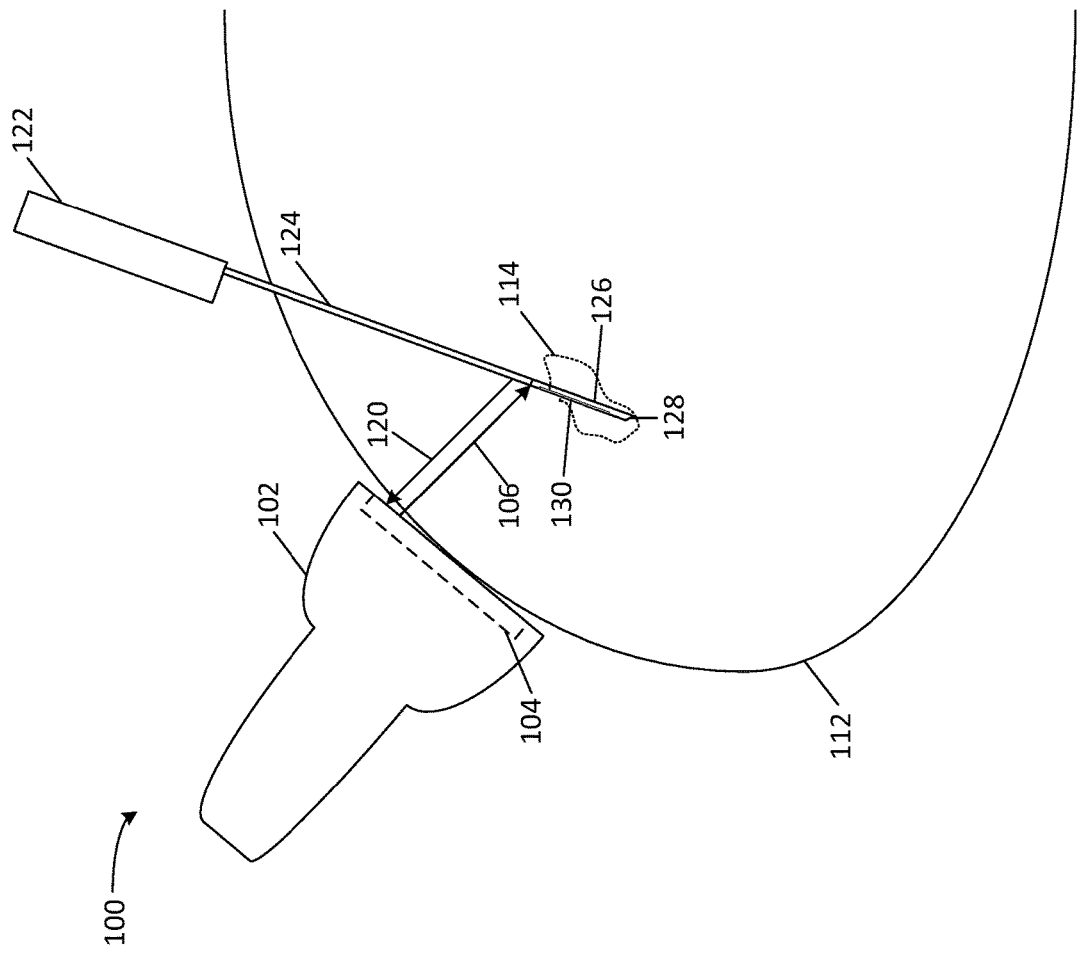
FIG. 1C depicts an example of the biopsy needle visualization system with the biopsy needle in a post-fire configuration.

FIG. 1C depicts an example of the biopsy needle visualization system 100 with the biopsy needle 124 in a post-fire configuration. The biopsy needle visualization system 100 as depicted in FIG. 1C is substantially the same as the biopsy needle visualization system 100 depicted in FIG. 1B, with the exception that the biopsy needle 124 is in a post-fire configuration. In the post-fire configuration, the biopsy needle has a throw portion 126 that has extended from the biopsy needle 124. In some examples, the throw portion 126 may be an inner cannula of the biopsy needle 124. The throw portion 126 also includes an aperture 130 for collecting tissue from the lesion 114. The aperture 130 is located between a biopsy needle tip 128 and the portion of the biopsy needle 124 from the pre-fire configuration of the biopsy needle 124.

As can be seen from FIGS. 1B-1C, the biopsy needle 124 is inserted into the patient in a direction towards the lesion 114. When the biopsy needle 124 in its pre-fire configuration reaches a particular point within the patient 112, the biopsy needle 124 is fired. The firing of the biopsy needle 124 is often triggered by pressing or otherwise manipulating a trigger located on the biopsy device 122. When the biopsy needle 124 is fired, the throw portion 126 extends from the biopsy needle 124. In the example depicted, it is desired that the aperture 130 of the throw portion 126 be located at the lesion 114 such that tissue sample from the lesion 114 may be collected. As discussed above, determining the proper location and positioning of the biopsy needle 124 in the pre-firing configuration to achieve the desired aperture 130 and tip 128 location in a post-firing configuration is both important and difficult. By generating ultrasound imagery during the biopsy procedure that includes the biopsy needle 124, analysis may be performed on the image to provide additional guidance as to the positioning of the needle, as discussed further below with reference to FIGS. 2-4.

Figure 1D:
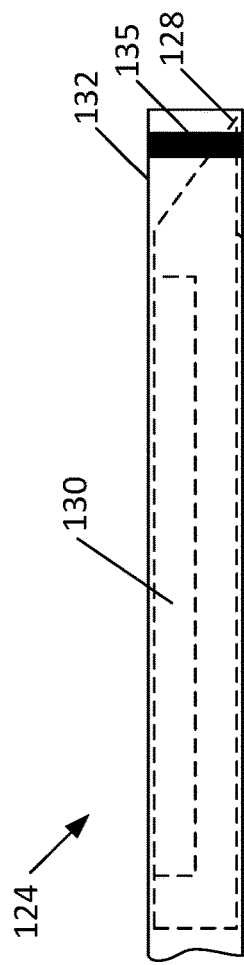
FIG. 1D depicts an example a biopsy needle in a pre-fire configuration.
Figure 1E:
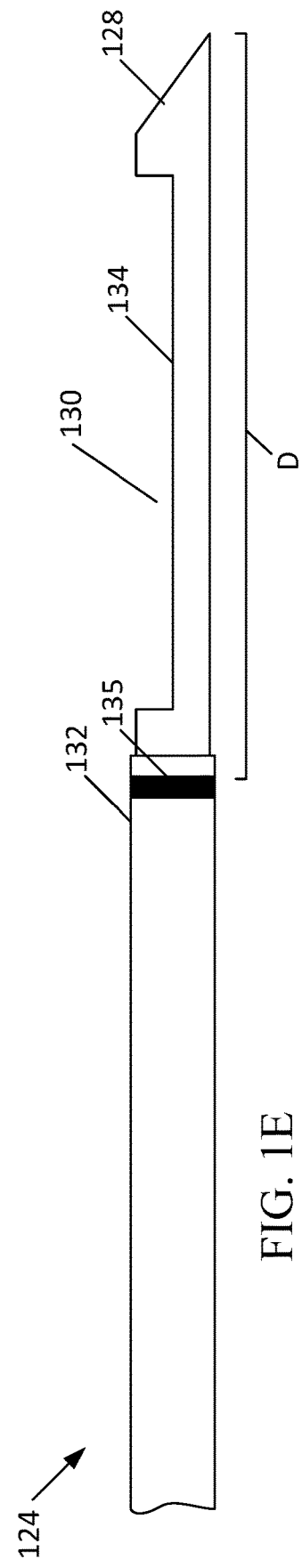
FIG. 1E depicts an example of the biopsy needle of FIG. 1D during a firing process.
Figure 1F:
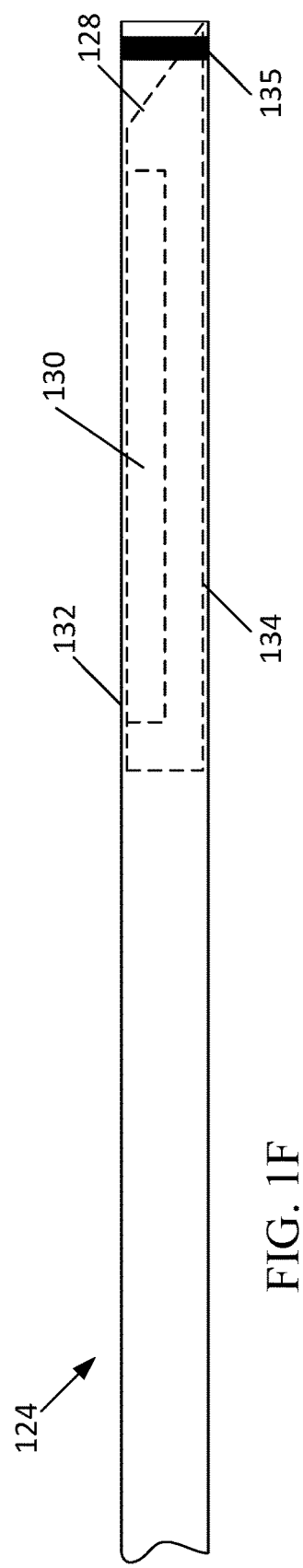
FIG. 1F depicts an example of the biopsy needle of FIGS. 1D-1E in a post-fire configuration.

FIGS. 1D-1F depict an example of biopsy needle 124 at multiple stages during the firing process and are discussed concurrently. In particular, FIG. 1D depicts the biopsy needle 124 in a pre-fire configuration, FIG. 1E depicts the biopsy needle 124 during the firing process, and FIG. 1F depicts the biopsy needle 124 in the post-fire configuration. The example biopsy needle 124 includes an outer cannula 132 and an inner cannula 134. The inner cannula 134 includes an aperture 130 and a biopsy needle tip 128. During the firing process, the inner cannula 134 advances from the outer cannula 132. The distance the inner cannula 134 extends from the outer cannula 132 may be referred to as the throw distance. Once the inner cannula 134 has extended from the outer cannula 132 (as depicted in FIG. 1E), tissue is captured in the aperture 130. In some examples, a vacuum mechanism may be attached to the biopsy needle 124 to pull tissue into the aperture 130. With the tissue captured in the aperture 130, the outer cannula 132 is advanced over the inner cannula 134 (as shown in FIG. 1F), which cuts the tissue thereby separating the tissue captured in the aperture 130 from remaining tissue of the patient. Both the outer cannula 132 (alone) or the outer cannula 132 and the inner cannula 134 may be manufactured, in whole or in part, from a material that displays a high degree of echogenicity, which causes those elements to appear brighter in a resulting ultrasound image. The biopsy needle 124 is then in a complete post-fire configuration and may be retracted from the patient 112. The tissue captured in the aperture 130 may then be removed from the biopsy needle 124 for further analysis and examination. The procedure described above may be performed a number of times to remove multiple biopsy samples. At the end of the biopsy procedure a marker marking the location of the biopsied site may be inserted into the biopsy location.

Another case, only a portion 135 of the outer cannula 132 is formed from a high-echogenicity material, which may completely or partially surround the circumference of the inner cannula. The portion 135 at a location on the outer cannula 132 that is a known distance D from the tip 128 of the inner cannula 134 when at its maximum extent. This distance D may be specific to a particular needle type or manufacturer, for example. Here, the known distance D locates the portion 135 distal from the tip 128, and opposite the aperture 130 therefrom, but other locations are contemplated. By forming only the portion 135 of the outer cannula 132 of a high echogenic material and a known distance D from the tip 128, accuracy of the post-fire location of the inner cannula 134 may be improved. More specifically, if a biopsy needle having an outer cannula formed completely from a high echogenic material is utilized, it may be unknown to the processor analyzing the image (or the surgeon performing the procedure) if the apparent tip of the outer cannula identified is the actual tip of that component. Given the depth of penetration of the ultrasound waves, it is possible that the apparent tip of the outer cannula may simply be a portion of the outer cannula located at the maximum depth of that wave penetration. In the configuration depicted in FIGS. 1D-1E, however, once the portion 135 is detected, the location of the actual tip 128 may be more easily determined.

Figure 1G:
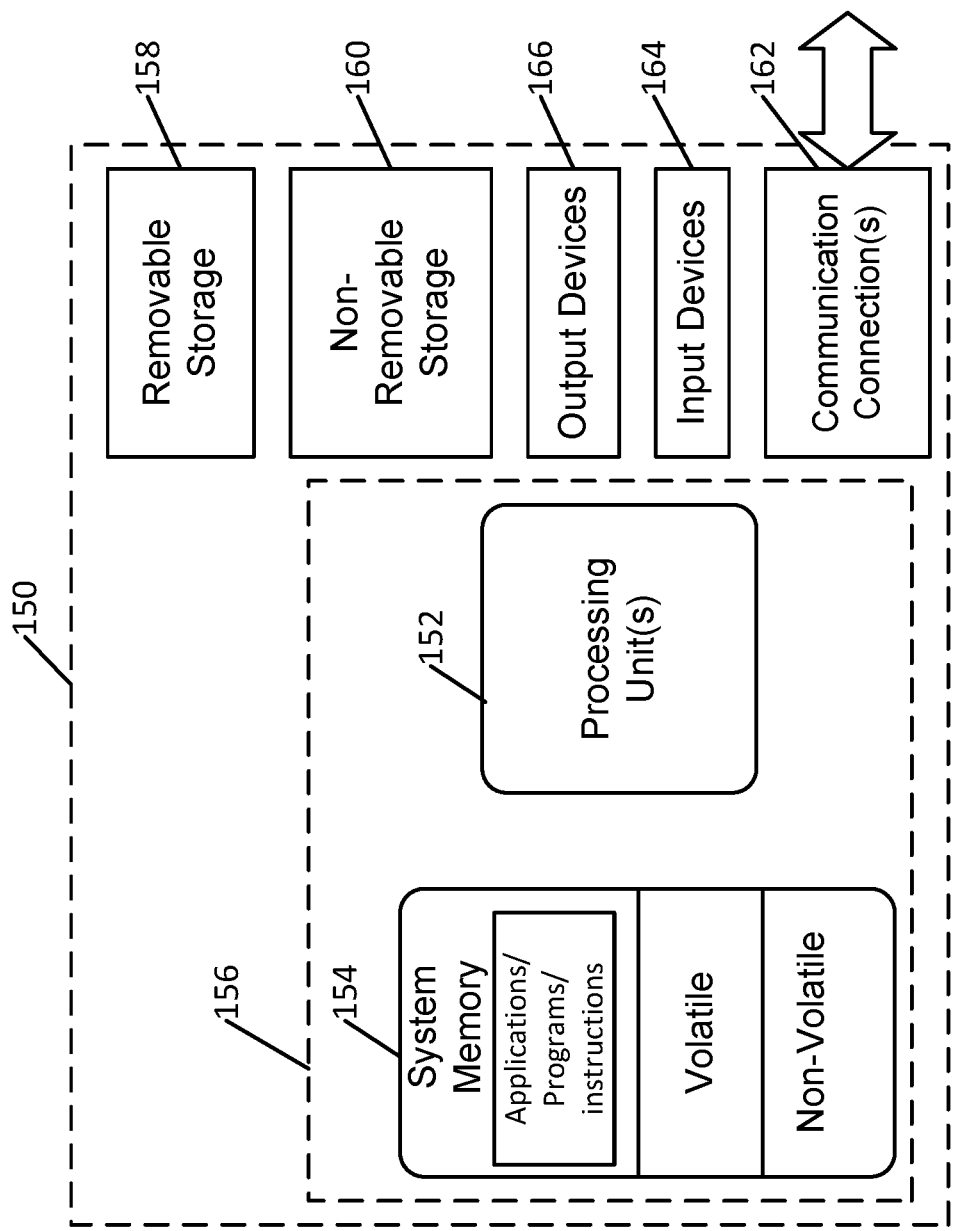
FIG. 1G depicts an example of a suitable operating environment for incorporation into the biopsy needle visualization system.

FIG. 1G depicts an example of a suitable operating environment 150 for incorporation into the biopsy needle visualization system 100. In its most basic configuration, operating environment 150 typically includes at least one processing unit 152 and memory 154. Depending on the exact configuration and type of computing device, memory 154 (storing instructions to perform the active monitoring embodiments disclosed herein) may be volatile (such as RAM), non-volatile (such as ROM, flash memory, etc.), or some combination of the two. This most basic configuration is illustrated in FIG. 1E by dashed line 156. Further, environment 150 may also include storage devices (removable 158, and/or non-removable 160) including, but not limited to, magnetic or optical disks or tape. Similarly, environment 150 may also have input device(s) 164 such as keyboard, mouse, pen, voice input, etc. and/or output device(s) 166 such as a display, speakers, printer, etc. The input devices 164 may also include circuitry or interfaces to receive or detect signals emitted from the various components of the biopsy needle visualization system 100, such as the ultrasound probe 102. Also included in the environment may be one or more communication connections 162, such as LAN, WAN, point to point, etc. In embodiments, the connections may be operable to facility point-to-point communications, connection-oriented communications, connectionless communications, etc.

Operating environment 150 typically includes at least some form of computer readable media. Computer readable media can be any available media that can be accessed by processing unit 152 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, microwave, and other wireless media. Combinations of the any of the above should also be included within the scope of computer readable media.

The operating environment 150 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media.

Figure 2:
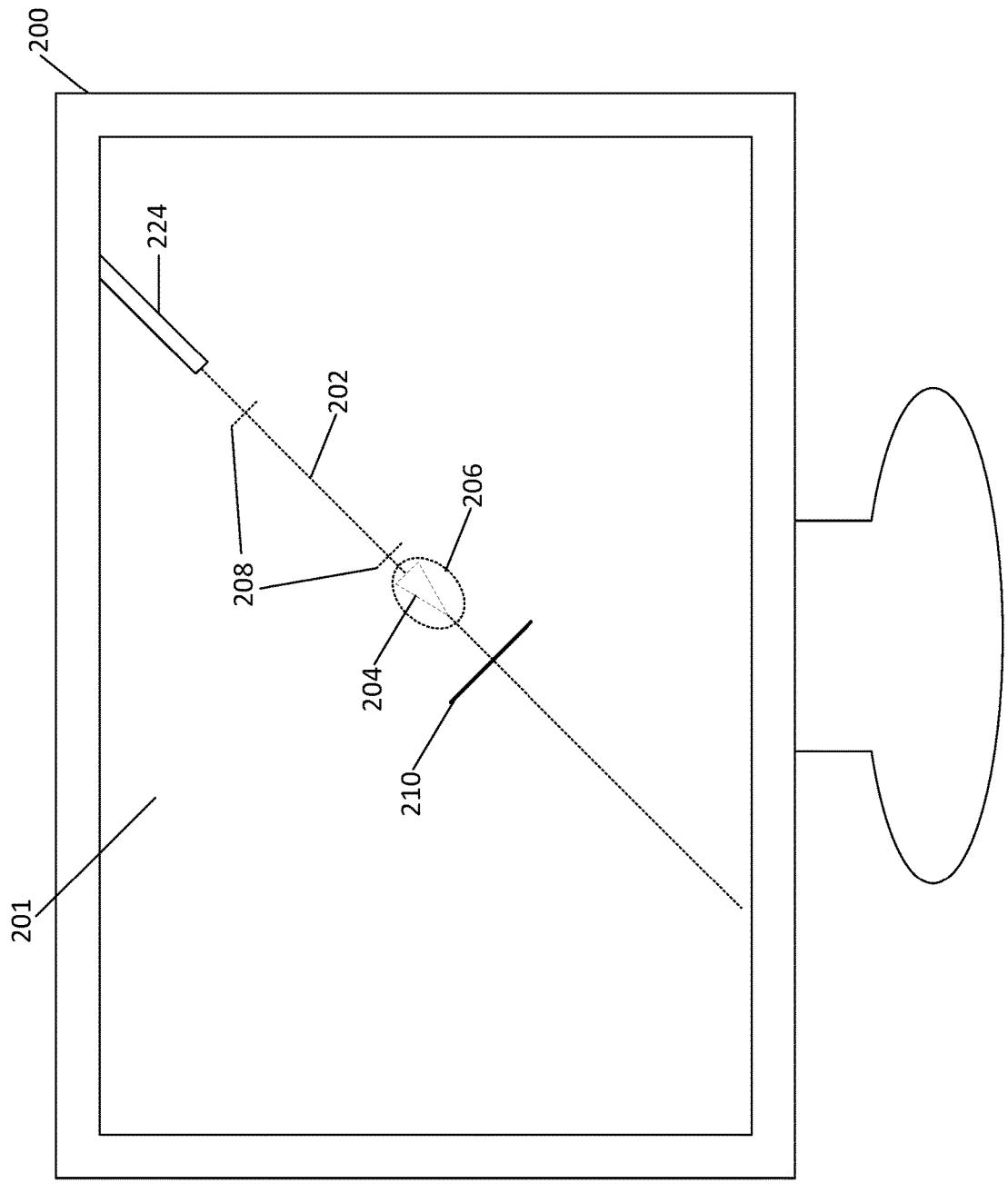
FIG. 2 depicts an example ultrasound image including biopsy needle prediction indicators.

FIG. 2 depicts an example of an ultrasound image 201 including a biopsy needle 224 and multiple biopsy needle prediction indicators. The ultrasound image is displayed on a display 200. The display 200 may be the display 110 discussed above with reference to FIG. 1A. The ultrasound image 201 is an example of an ultrasound image where the biopsy needle 224 is within the field of view of the ultrasound probe. The ultrasound image 201 is generated from image data generated from the detected reflected ultrasonic sound waves. Based on the image data or the ultrasound image 201, the biopsy needle 224 may be identified through the use of image analysis techniques. The shape of the biopsy needle 224 is generally distinguishable from the other tissue or internal portions of the human body. For instance, the biopsy needle 224 has shape that is not naturally occurring in the human body. Further, the material of the biopsy needle 224 may also be manufactured in whole or in part from a material that makes the marker easier to detect within the ultrasound image 201 or image data. For instance, at least a portion of the material of the biopsy needle 224 may be a material that has a high degree of echogenicity, which causes that portion of the biopsy needle 224 to appear brighter in the resulting ultrasound image 201. Air or other gas within the biopsy needle may also cause the biopsy needle 224 to appear brighter in the ultrasound image 201.

Accordingly, based on the distinguishing shape and material of the biopsy needle 224, image analysis techniques may more easily identify the biopsy needle within the ultrasound image 201. The image analysis techniques may also be based on machine learning techniques, such as neural networks, deep learning algorithms, statistical analysis techniques, enhanced contrast techniques, or other pattern recognition or matching techniques that are trained based on the shape of the biopsy needle. As an example, the image analysis algorithms may first be trained on a set of ultrasound images containing a particular type of biopsy needle 224. The current ultrasound image 201 or image data is then provided as an input into the trained image analysis algorithms to detect or identify the biopsy needle 224. Identifying the biopsy needle 224 may be based on the cross-section of the biopsy needle 224 as the ultrasound image 201 is a two-dimensional image with a cross-section of the biopsy needle 224.

In additional examples, an ultrasound technician, surgeon, or other user may provide additional input to assist in the identification of the biopsy needle 224 in the ultrasound image 201. For example, input may be provided indicating the type of biopsy needle that is being used for the biopsy procedure. In an example, the input may include providing a model number, make, or other identifying information for the biopsy needle 224. Based on the input from the user, the system may obtain the dimensions and other information about the biopsy needle 224, such as from a local or remote database storing such information. The local or remote database may be preprogrammed with several biopsy needle models, makes or types and include the associated geometries associated with the biopsy needles. The dimensions of the biopsy needle 224 may then be used by the image analysis techniques to assist in identification of the biopsy needle 224 within the ultrasound image 201. The additional input from the ultrasound technician, surgeon, or other user may also include directly identifying the biopsy needle on the ultrasound image 201, such as receiving pointer, touch, or other input to locate the biopsy needle 224. For instance, the ultrasound technician may select the biopsy needle 224 by clicking on the biopsy needle 224 with a mouse on a display of the ultrasound image. The input identifying the biopsy needle 224 (such as click on the image of the biopsy needle 224) may also be utilized in the image analysis techniques to limit the area of the ultrasound image 201 to be analyzed. For example, upon receiving a selection of the biopsy needle 224 from an ultrasound technician, a predetermined area around the selection point may be analyzed to identify the biopsy needle 224. In other examples, two-dimensional input (such as box) may be provided by the ultrasound technician to provide a boundary for an area that is to be analyzed by the image analysis techniques to identify the biopsy needle 224. In other examples, a combination of both user input on the display of the ultrasound image and image analysis techniques may be used to determine the biopsy needle 224.

Once the biopsy needle 224 is identified in the ultrasound image 201, biopsy needle prediction indicators may be generated based on the predicted location of the biopsy needle 224 after firing. The biopsy needle prediction indicators indicate the predicted location of the biopsy needle 224 and the elements thereof after firing of the biopsy needle 224. For example, when the biopsy needle 224 is fired, the biopsy needle 224 may deflect before coming to rest in its post-fire configuration state. The deflections of the biopsy needle 224 is based in part on the properties of the biopsy needle 224 along with the characteristics or properties of the tissue through which the biopsy needle 224 passes during firing. The predicted locations of the elements of the biopsy needle 224 represented by the biopsy needle prediction indicators are determined in light of the biopsy needle 224 properties and/or the tissue characteristics, as discussed further below.

For example, breast tissue comprises glandular, connective, and fat tissue. Patients undergoing breast biopsy may have differing relative amount of these different types of breast tissue. For example, dense breasts have relatively high amounts of glandular tissue and fibrous connective tissue and relatively low amounts of fatty breast tissue. On the other side of the spectrum, a breast may be predominately made of fatty breast tissue. Other characteristics of breast tissue may include scattered areas of dense glandular tissue and fibrous connective tissue and heterogeneously dense breast tissue with many areas of glandular tissue and fibrous connective tissue. Different characteristics of breast tissue may result in different locations for the prediction indicators for the biopsy needle 224. In one example, breast tissue having higher degrees of density or stiffness may result in more deflection of the biopsy needle 224 when the biopsy needle 224 passes through the breast tissue during firing. The characteristics of the breast tissue may be determined through image analysis and/or input from a user indicating the characteristics of the breast tissue. Portions of breast tissue may be highlighted or otherwise emphasized in the ultrasound image. For instance, if a particularly dense or stiff portion of tissue is identified through image analysis and/or user input, that portion of tissue may be highlighted or otherwise emphasized on the ultrasound image to alert the medical professional to the existence of the tissue.

The biopsy needle prediction indicators include a trajectory indicator 202, a tip indicator 204, a deflection probability indicator 206, aperture indicators 208, and a maximum needle depth indicator 210. The trajectory indicator 202 indicates the trajectory of the biopsy needle 224. For instance, if the biopsy needle 224 was fired in its current position in the ultrasound image 201, the throw portion of the biopsy needle 224 is predicted to follow the line of the trajectory indicator 202. As depicted in FIG. 2, the trajectory indicator 202 may be displayed as line extending from the biopsy needle 224 and extending substantially parallel to the biopsy needle 224. The tip indicator 204 indicates the most likely position of the tip of the biopsy needle 224 in its post-fire configuration. For example, if the biopsy needle 224 were fired from its current position in the current ultrasound image 201, the most likely location for the tip of the biopsy needle 224 in the post-fire configuration is shown by the tip indicator 204. The biopsy needle 224 may be in the shape of a triangle or have a shape that more closely resembles a tip shape of a current biopsy needle 224 being used for the procedure. For instance, the shape of the tip indicator 204 may be based on the geometry of the tip of the biopsy needle 224 being used for the biopsy. Accordingly, the shape of the tip indicator 204 may change based on the particular biopsy needle 224 being used to perform the biopsy. Other shapes for the tip indicator 204 are also possible, including lancet tip needle, trocar tip needle, bevel tips, and multiple point tips, among others. A deflection probability indicator 206 is also displayed adjacent to the tip indicator 204. The deflection probability indicator 206 indicates a range for a predicted post-fire tip location based on a determined deflection probability for the biopsy needle 224. For example, the tip indicator 204 may indicate the most likely predicted position for the tip of the biopsy needle 224, and the deflection probability indicator 206 may encompass all possible predicted locations for the tip of the biopsy needle 224. In other examples, the deflection probability indicator 206 may encompass a significant portion of the possible predicted tip locations, such as 80% likelihood or the predicted tip locations within one or two standard deviations from the most likely tip location. The deflection probability indicator 206 may be in the shape of an ellipse, a circle, square, rectangle, or other shape. The deflection probability indicator 206 may also be in the form of a heatmap showing the probability distribution for the predicted tip location.

The aperture indicators 208 indicate the predicted location for the aperture of the biopsy needle 224 in its post-fire configuration. By seeing the predicted location for the aperture represented by the aperture indicators 208, a surgeon is able to more accurately predict if the aperture will be in the targeted location (e.g., a lesion or mass) after the biopsy needle 224 is fired. The aperture indicators 208 may be represented by two line segments that are perpendicular to the trajectory indicator 202. The distance between the aperture indicators 208 represents the length of the aperture of the particular biopsy needle 224 that is being used to perform the biopsy. Accordingly, the distance between the aperture indicators 208 may change for different biopsy needles.

The maximum needle depth indicator 210 indicates a maximum depth the biopsy needle 224 may extend in its pre-fire configuration where a prediction for the tip location may still be made. For instance, if the biopsy needle 224 in its pre-fired configuration were to pass the maximum needle depth indicator 210, the tip of the biopsy needle 224 would be outside the current ultrasound image 201. The maximum needle depth indicator 210 may be a line segment that is perpendicular to the trajectory indicator 202. While the biopsy needle prediction indicators have been described and depicted as having certain shapes or orientations, other shapes and orientations are also contemplated herein. For instance, while some of the indicators are displayed in dashed lines and others in solid lines, the technology is not limited to such examples.

Figure 3A:
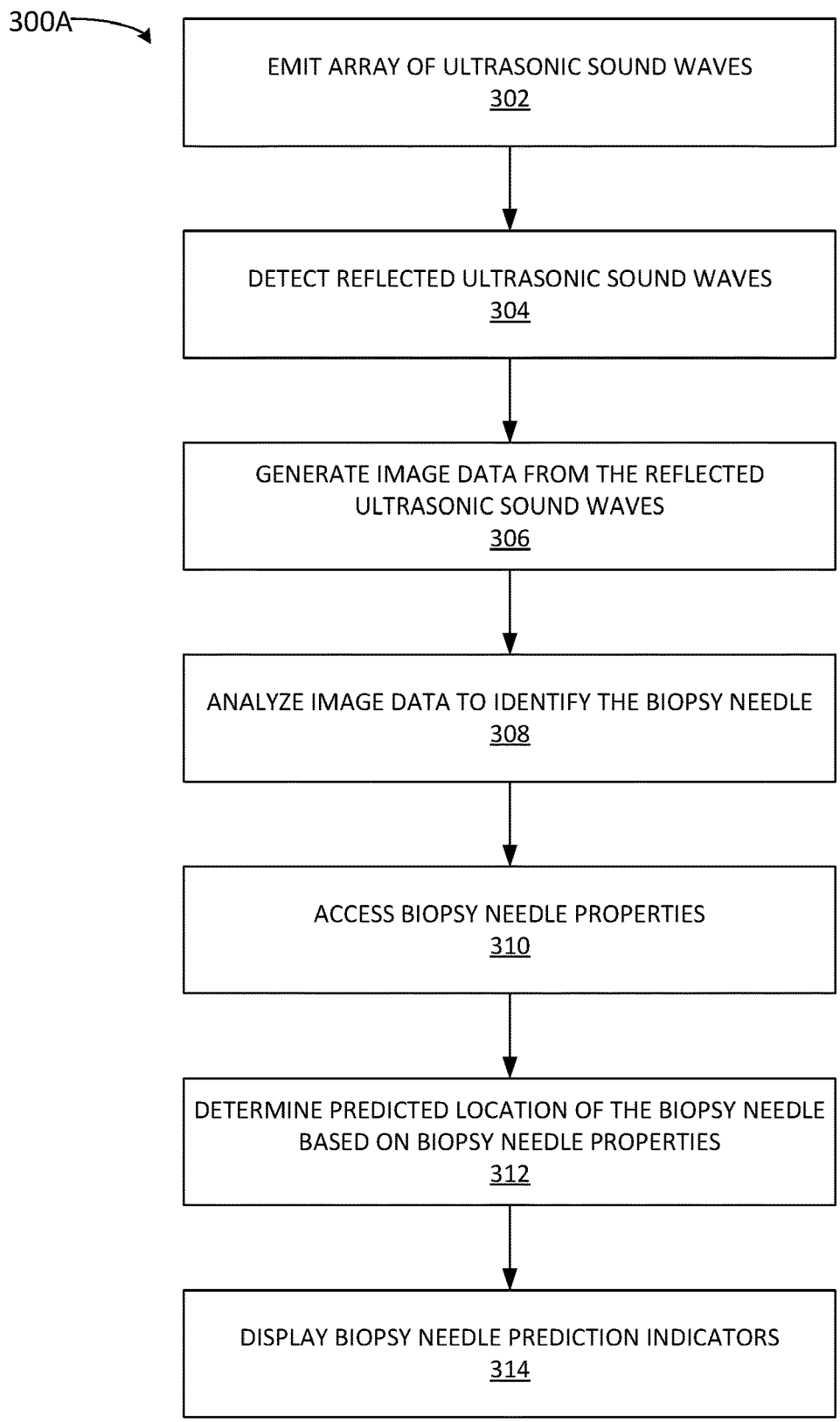
FIG. 3A depicts an example method for visualization of a biopsy needle.

FIG. 3A depicts an example method 300A for predictive visualization of a biopsy needle. The predictive visualization method 300A provides for additional guidance and biopsy needle prediction indicators to be displayed on ultrasound as a biopsy is being performed. As such, a surgeon performing the biopsy is able to receive substantially real-time guidance for performing the biopsy. The operations of method 300A and the other methods discussed herein may be performed by at least one processor in conjunction with other components of a suitable operating environment, such as the operating environment 150 in FIG. 1G, within a system such as system 100 depicted in FIGS. 1A-1C.

At operation 302, an array of ultrasonic sound waves are emitted from an ultrasonic transducer of an ultrasound probe. The ultrasound waves enter the interior of the patient and are reflected from the components of the interior of the patient, including natural tissue as well as the biopsy needle, as discussed above. The reflected ultrasonic waves are then detected at operation 304. At operation 306, ultrasound image data is then generated from the detected reflected ultrasonic sound waves. The ultrasound image data may be B-mode ultrasound imaging data.

At operation 308, the image data is analyzed by a processor of the biopsy needle visualization system to identify or detect the biopsy needle within the image data. As discussed above, the image analysis techniques may be based on image processing techniques, and machine learning techniques, such as neural networks, deep learning algorithms, or other pattern matching techniques, that are trained based on the shape of the marker implanted in the patient. As an example, the image analysis algorithms may first be trained on a set of ultrasound images containing the biopsy needle in different orientations and views. A current ultrasound image or image data is then provided as an input into the trained image analysis algorithms to detect or identify the biopsy needle. Identifying the marker may generally be based on the shape and dimensions of the biopsy needle.

At operation 310, properties for the biopsy needle are accessed or otherwise determined. The properties for the biopsy needle at least one of a needle length, a needle gauge, a needle wall thickness, a needle material composition, a needle tip geometry, and a needle firing mechanism property, aperture length, throw length, among other potential biopsy needle properties. The properties for the biopsy needle may be accessed by querying a database stored locally in the biopsy needle visualization system 100 or a remote database accessible from the biopsy needle visualization system 100. In an example, a user interface may first be displayed at the beginning of a biopsy procedure to allow for a selection or input a type of biopsy needle to be used in the biopsy procedure. In an example, the input into the user interface may indicate a particular make or model of the biopsy needle. In such an example, the input into the user interface may be used to query the respective database to access or determine the properties for the biopsy needle indicated by the input into the user interface. In other examples, the properties of the biopsy needle (e.g., needle length, gauge, etc.) are provided directly as input into the user interface. In such an example, no database query is performed as the properties have already been provided directly.

At operation 312, the predicted location of the biopsy needle is determined. Determining the predicted location of the biopsy needle may be include determining the location of the aspects or portions of the biopsy needle, such as the needle tip, the aperture, the throw portion, or other features of the biopsy needle. For example, the location of the biopsy needle in a post-fire configuration may be determined. In such an example, the various aspects of the biopsy needle, such as the needle tip, aperture, throw portion, and/or other features, aspects, or portions of the biopsy needle, may be determined for needle in the post-fire configuration. The determination of the predicted location of the biopsy needle may be based on the biopsy needle properties accessed or determined in operation 310. In addition, the determined predicted location for the biopsy needle may be based on tissue properties as well. At operation 314, biopsy needle prediction indicators are displayed on an ultrasound image. For example, the biopsy needle prediction indicators may include one or more of a trajectory indicator, a tip indicator, a deflection probability indicator, aperture indicators, and a maximum needle depth indicator. Displaying the prediction indicators may also include changing the state of the prediction indicators. For instance, as the biopsy needle in its pre-fire position is moved within the patient, the state of the prediction indicators may change. As an example, the displayed location of the prediction indicators may change as the biopsy needle is repositioned. The prediction indicators may also include audible indicators or tactile indicators in the biopsy device. Additional details regarding the determination of the predicted location of the biopsy needle are discussed below with reference to FIGS. 3B and 3C.

In addition to the prediction indicators, additional positioning indicators may be displayed indicating to the medical professional how to alter the position of the biopsy needle to more accurately target the lesion or area of interest. For instance, the lesion or area of interest may be identified through image analysis and/or user input. If the predicted location of the biopsy needle aperture is not aligned with the lesion, positioning indicators may be displayed to guide the medical professional on how to move the needle into a position where the predicted location of the needle aperture more accurately targets the lesion. Such positioning indicators may be in the form of arrows and/or text, among other indicators, that provide the positioning guidance. In addition, visual, tactile, and/or audible positioning indicators may be displayed that indicate proper positioning of the biopsy needle. As an example, when the needle is positioned such that the aperture of the needle will properly target the lesion, tactile, audible, and/or visual feedback may be provided. For instance, an audible sound may be provided, and the sound may change volume or frequency as the biopsy needle is moved toward or away from properly targeting the lesion or area of interest.

Figure 3B:
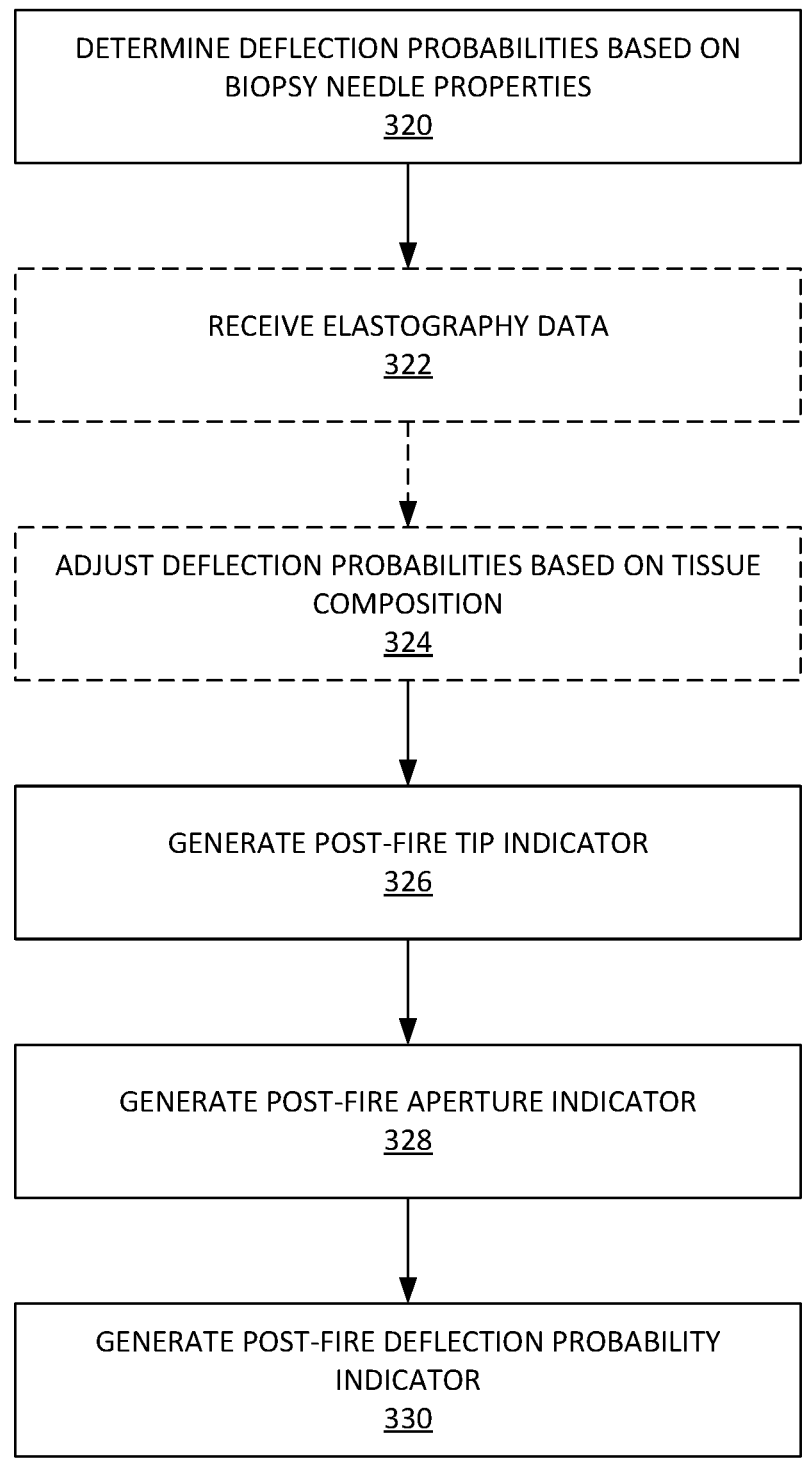
FIG. 3B depicts another example method for visualization of a biopsy needle.

FIG. 3B depicts another example method 300B for predictive visualization of a biopsy needle. At operation 320, deflection probabilities for the particular biopsy needle being used in the biopsy procedure are determined based on the properties for the particular biopsy needle. When a biopsy needle is fired, the throw portion may deflect due to the internal tissue of the patient. The direction and amount of deflection is based on the biopsy needle properties as well as the type of tissue that the biopsy needle passes through when fired. As discussed above, the biopsy needle properties may include one or more of a needle length, a needle gauge, a needle wall thickness, a needle material composition, a needle tip geometry, and a needle firing mechanism property, aperture length, throw length, among other potential biopsy needle properties. Each of these properties may have an effect on the deflection of the biopsy needle when fired. For example, a biopsy needle with a long length, but a large gauge (i.e., small diameter) may be more likely to deflect when fired. Similarly, needles with thinner wall thicknesses may also be more likely to have a greater degree of deflection. The geometry of the tip of the biopsy needle also affects the amount of deflection as well as the direction of deflection. The firing mechanism properties of the biopsy needle further affect the deflection due to the force with which the needle is fired. The other properties of the biopsy needle may also have effects on the magnitude and/or direction of the deflection of the biopsy needle.

The deflection probabilities of the biopsy needle may be determined analytically and/or be based on a set of experimental data. For instance, based on the properties of the needle, a mathematical prediction may be made as to the probability of the final needle position and its deflection. The mathematical prediction may be based on the mechanical behavior of a hollow cylinder advancing through a material having a density and/or stiffness similar to that of human tissue at the biopsy site. The properties of the hollow cylinder or tube may be modified based on the properties of the biopsy needle and the resultant flex of the hollow cylinder or tube. Computerized simulations for the biopsy needle may also be processed to determine the probabilities of the biopsy needle deflection. The results of the computerized simulations provide the deflection probabilities for the biopsy needle. The deflection probabilities may also be determined empirically a set of experimental results. For example, a biopsy needle may be inserted into a replica of a breast (or other human tissue particular to the biopsy site) and fired. The deflection of the needle may be tracked using the biopsy needle visualization system. The testing may be repeated form an experimental data set for different biopsy needles. For example, experimental data may be generated for a needle passing through dense tissue and for a needle passing through adipose tissue. The deflection properties for a particular biopsy needle may be determined from the experimental data set.

At operation 322, elastography data is optionally received. The elastography data may be elastography data for the tissue along the fire trajectory for the biopsy needle (e.g., the path along which the biopsy needle will pass when fired). The elastography data may be obtained directly from the biopsy needle visualization system. As an example, the imaging mode of the ultrasound components may be include an elastography mode that provides elastography data indicated the stiffness or other elastic properties of the tissue. The elastography data may be received from other sources as well based on known tissues at the biopsy site. In one example, a fire trajectory may be determined in part based on ultrasound image data, and the fire trajectory may have already been determined for the trajectory indicator. Elastography data is then received for at least a portion of the tissue along the fire trajectory. Based on the elastography data received, tissue properties may be determined for the tissue along the fire trajectory.

At operation 324, tissue properties of the patient may be used to adjust the deflection probabilities. The tissue characteristics may be tissue characteristics along the fire trajectory for the needle or general tissue characteristics for the biopsy site. In some examples, the tissue characteristics are determined for a predetermined distance around the fire trajectory. The tissue properties may be determined from the elastography data received or captured in operation 322, image analysis of an ultrasound image, and/or user input. For example, where the elastography data indicates that there is a stiff portion of tissue within the biopsy needle fire trajectory, deflection may be more likely to occur. The deflection probabilities may then be updated based on the stiffness of the portion of the tissue and/or the location of the portion of the tissue. Other tissue properties, such as density and/or tissue composition, may also be incorporated to adjust the deflection probabilities. In an example, such tissue properties may be identified through image analysis of the ultrasound image. For example, tissue characteristics may be determined for a portion of tissue appears brighter in the ultrasound image and/or has a particular shape. In addition, a user may also provide input that identifies a portion of tissue and provides tissue characteristics (such as density, stiffness, etc.) for the identified tissue. The user input and/or image analysis may also identify the type of tissue in the ultrasound image. For example, the user input and/or image analysis may identify portions of tissue as either glandular tissue, connective tissue, or fat tissue. The tissue characteristics for the type of tissue may then be accessed or received, such as from a local or remote database, and those tissue characteristics may then be used in determining the deflection probabilities. The tissue properties may also be incorporated directly into the probability deflection determination in operation 320.

At operation 326, a tip indicator is generated based on the deflection probabilities and the properties for the biopsy needle. The tip indicator may be for the biopsy needle in its post-fire configuration. For example, based on the length of the throw portion for the particular needle and the deflection probabilities, the predicted location for the tip of the biopsy needle in the post-fire configuration may be determined, and the tip indicator may be generated based on that determination. At operation 328, an aperture indicator (or aperture indicators) may be generated based on the deflection probabilities and the properties for the biopsy needle. The aperture indicator may be for the biopsy needle in its post-fire configuration. For example, based on the length of the throw portion, the aperture location, and the deflection probabilities, a predicted location for the aperture of the biopsy needle in the post-fire configuration may be determined. The aperture indicator may be generated based on that determination. At operation 330, a deflection probability indicator is generated. The deflection probability indicator may be for the tip of the biopsy needle in its post-fire configuration. The deflection probability indicator is based on the determined deflection probabilities. The deflection probability indicator indicates a range for a predicted post-fire tip location based on a determined deflection probability for the biopsy needle. For example, the tip indicator may indicate the most likely predicted position for the tip of the biopsy needle, and the deflection probability indicator may encompass all possible predicted locations for the tip of the biopsy needle. In other examples, the deflection probability indicator may encompass a significant portion of the possible predicted tip locations, such as 90%, 80%, or 70% likelihood or the predicted tip locations within one or two standard deviations from the most likely tip location. To show the probability distribution for the determined deflection probabilities, the deflection probability indicator may also be in the form of a heatmap.

Figure 3C:
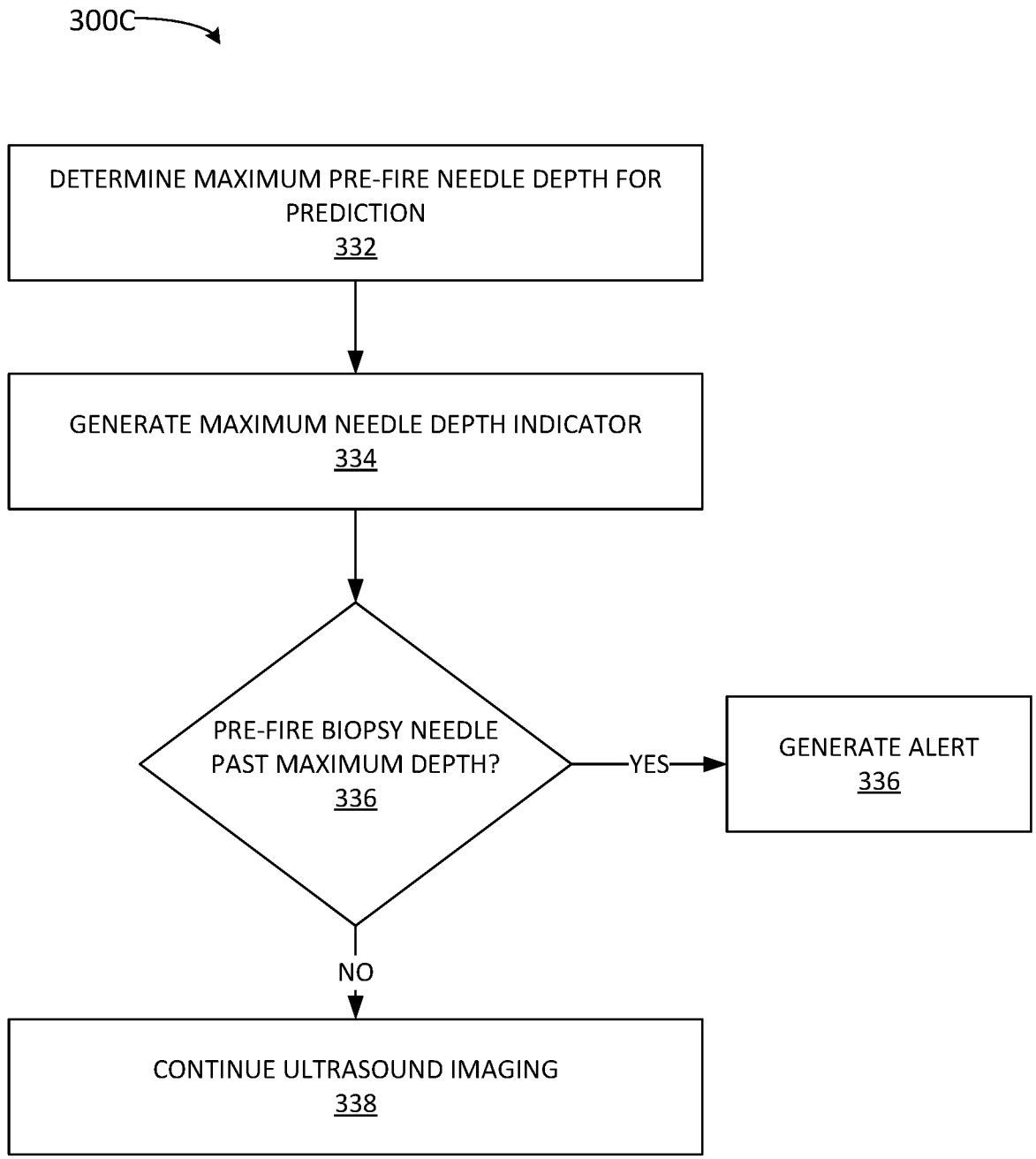
FIG. 3C depicts another example method for visualization of a biopsy needle.

FIG. 3C depicts another method 300C for predictive visualization of a biopsy needle. At operation 332, a maximum pre-fire biopsy needle depth for prediction is determined. The maximum pre-fire biopsy needle depth is a maximum depth the biopsy needle may extend in its pre-fire configuration where a prediction for the tip location may still be made. The determination of the maximum pre-fire biopsy needle depth may be based on the predicted tip location and the size of the display displaying the ultrasound image. Based on the determined maximum pre-fire biopsy needle depth, a maximum needle depth indicator is generated and may be displayed in the position of the determined maximum pre-fire biopsy needle depth.

At operation 336, a determination is made as to whether the biopsy needle in its pre-fire configuration has passed the maximum pre-fire biopsy needle depth. If the biopsy needle has passed the maximum pre-fire biopsy needle depth, the method 300C flows to operation 336 where an alert is generated that alerts the surgeon a tip location predication can no longer be presented on the screen. The alert may be visual, audible, or tactile. In an example, an audible or tactile indicator may be also provided that changes frequency or amplitude as the biopsy needle approaches the maximum pre-fire biopsy needle depth. Accordingly, based on the changing state of the indicator, the medical professional may be provided continuous guidance as to the positioning of the biopsy needle. If the biopsy needle depth has not passed the maximum pre-fire biopsy needle depth, ultrasound imaging continues and the maximum pre-fire biopsy needle depth indicator remains displayed for visual reference for the surgeon.

Although FIGS. 3A-C describe methods 300A-C for visualization of a biopsy needle, these methods 300A-C may be implemented for visualization of any device to be positioned along an imaging plane, as required or desired. For example, the methods 300A-C may be used to visualize a needle, an introducer, a wire, etc. to determine movement and/or deflection and/or diversion along or relative to a plane (e.g., an imaging plane of an ultrasound imager).

Figure 4:
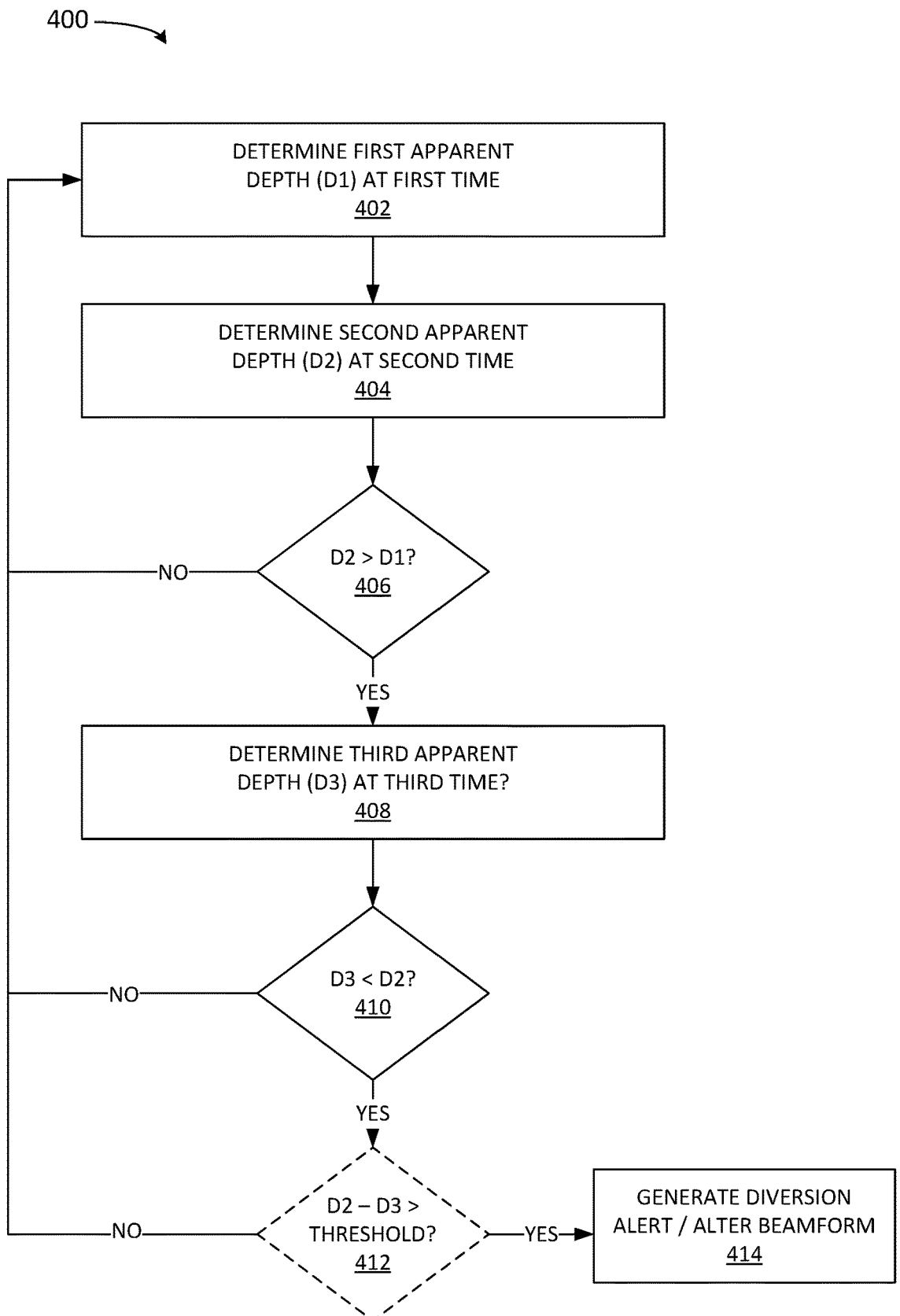
FIG. 4 depicts an example method for detecting plane diversion of a biopsy needle.

FIG. 4 depicts an example method 400 for detecting plane diversion of a biopsy needle. In an ultrasound image, the biopsy needle can be seen to advance to further depths into the patient when the biopsy needle is substantially aligned with the imaging plane of the ultrasound imaging system. If the needle diverts out of the imaging plane, the needle appears in the ultrasound image to no longer be advancing, despite the needle actually moving further into the patient. In some instances, a reduction in the apparent depth of the needle may be seen in the ultrasound image. If the reduction in apparent depth does not correspond with the needle being retracted from the patient, it is likely that the surgeon has diverted the needle out of the imaging plane and may need to readjust either the needle or the ultrasound imaging probe. Method 400 provides an alert or a change in beamform from the ultrasound imaging probe as a result to such a diversion of the needle out of the imaging plane.

At operation 402, a first apparent depth (D1) for the biopsy needle is determined at a first time (t1). The apparent depth of the biopsy needle is the depth of the biopsy needle into the patient as it appears in the ultrasound image. In some examples, the apparent depth of the needle may be determined by measuring the length of the portion of the biopsy needle that appears in the ultrasound image. At operation 404, the apparent depth of the needle is determined again at a subsequent time (t2). This subsequent apparent depth is a second apparent depth (D2). At operation 406, a determination is made as to whether D2 is greater than D1. If D2 is not greater than D1, the needle may not be advancing or may be being retracted. As such, the method 400 returns to operation 402 where the method 400 repeats. If D2 is greater than D1, the needle is likely advancing into the patient on the imaging plane, and the method 400 flows to operation 408. At operation 408, a third apparent depth (D3) is measured at a time (t3) subsequent to the time (t2). At operation 410 a determination is made as to whether D3 is less than D2. If D3 is greater than D2, the needle is still advancing and in the imaging plane, and method 400 returns to operation 402 where method 400 repeats. If D3 is less than D2, either the needle has diverted out of the imaging plane or has been retracted. If D3 is less than D2, method 400 flows to optional operation 412, where the difference between D3 and D2 are compared to determine if the difference exceeds a threshold value. By comparing the difference between D3 and D2 to a threshold, false alarms may be avoided where only minor shifts in apparent depth are observed. If the different between D2 and D3 is less than the threshold, the method 400 flows back to operation 402 where method 400 repeats. If the difference between D2 and D3 exceeds the threshold, the method 400 flows to operation 414 where a diversion alert may be generated. The diversion alert indicates that the needle may have diverted out of the imaging plane for the ultrasound image. The diversion alert allows the surgeon to reposition the needle or the ultrasound probe to bring the needle back in line with the imaging plane. The surgeon may also ignore or silence the alert if the needle is actually being retracted from the patient. In addition, positioning indicators may be displayed indicating to the medical professional how to alter the position of the biopsy needle to bring the biopsy needle back into the imaging plane. For instance, if the needle has diverted out of the imaging plane, a positioning indicator may be displayed in operation 414. The positioning indicator may be in the form of arrows and/or text, among other possible indicators, that provide guidance to the medical professional as to how the needle should be moved to bring the needle back into the imaging plane.

At operation 414, the beamform of ultrasound waves emitted from the ultrasound probe may also be altered to alter the imaging plane. For instance, by altering the beamform of the ultrasound waves, the direction of the waves may be altered to modify the resultant imaging plane. When a potential diversion is detection (such as D3 being less than D2), the beamform may be altered. The alteration of the beamform may be predetermined based on the movement of the needle, or the beamform may change until an apparent depth for the needle can be determined that is greater than D2.

Although FIG. 4 describes a method 400 for detecting plane diversion of a biopsy needle, this method 400 may be implemented for determining plane diversion of any device to be positioned along a plane, as required or desired. For example, the method 400 may be used to detect plane diversion for a needle, an introducer, a wire, etc. to determine movement along a plane (e.g., an imaging plane of an ultrasound imager).

Devices other than biopsy needles, such as localization wires are also subject to significant challenges during insertion and placement. The present technology is also capable of assisting during the insertion and placement of such materials and devices for localization. Unlike a biopsy needle, some localization wires may have two-dimensional or three-dimensional characteristics that add additional complications in placement. For example, the present technology may provide guidance for a ring-based localization wire, such as the PERL® Ring Localization Device from Hologic Inc. of Marlborough, Massachusetts Placement of a two-dimensional or three-dimensional shape presents challenges for placement within a coordinate system (e.g., x-y-z coordinates) as well as challenges for rotational orientation within the coordinate system. The present technology provides solutions for such additional complexities by analyzing the position and orientation of the introducer to provide for a multi-dimensional prediction of the post-deployment location of the non-linear localization wire.

Figure 5A:
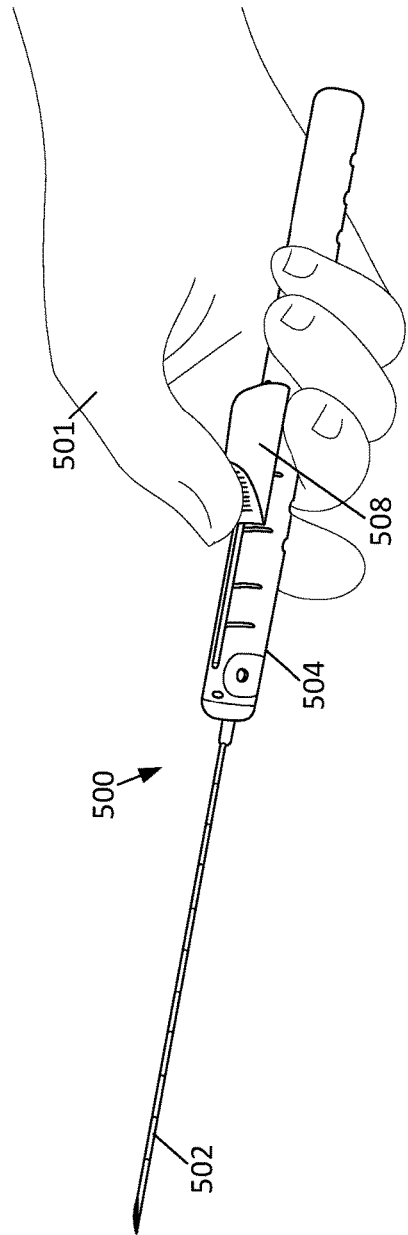
FIG. 5A depicts an example localization insertion device in a pre-deployment state for subcutaneous insertion of a localization wire.
Figure 5B:
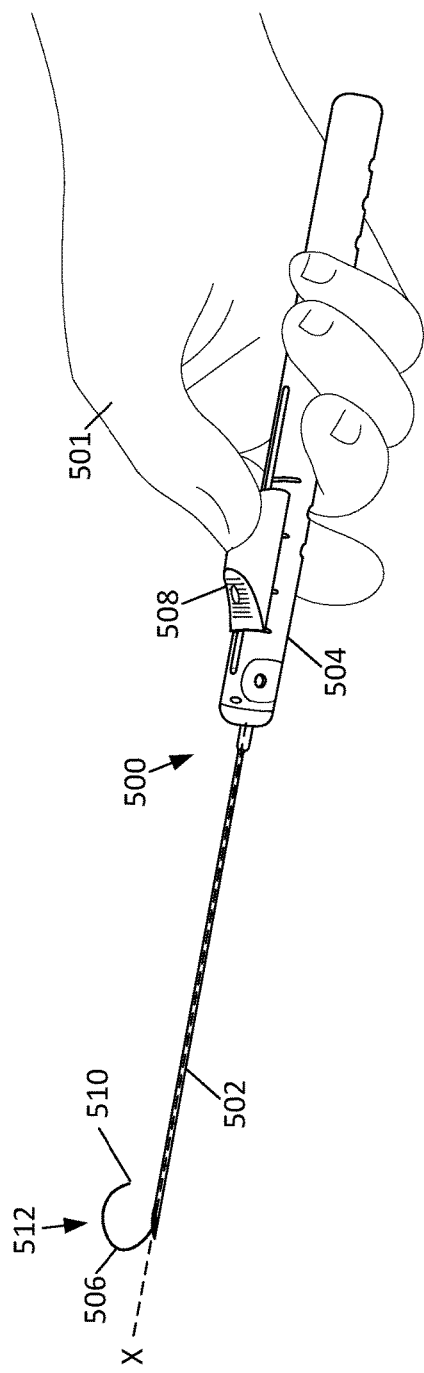
FIG. 5B depicts an example localization insertion device in a post-deployment state for subcutaneous insertion of a localization wire.

FIGS. 5A-B depict an example localization insertion device 500 in two states. One example of a localization insertion device 500 is the PERL® Ring Localization Device. FIG. 5A depicts an example localization insertion device 500 in a pre-deployment state for subcutaneous insertion of a localization wire 506. The localization insertion device 500 may be operated by a medical professional 501 to place the localization wire 506 in a patient to indicate a position of a lesion for surgical removal. The localization insertion device 500 includes an introducer 502 and a handle 504. The introducer 502 is configured to allow the medical professional 501 to insert the localization wire 506 into the patient. For example, the introducer 502 may include an annulus at which the localization wire 506 is fed through the introducer 502 for placement in the patient. The introducer 502 may be coupled to the handle 504 at a fixed position.

In the pre-deployment state shown in FIG. 5A, the localization wire 506 is coupled to the localization insertion device 500 such that the localization wire 506 moves with movement of the introducer 502 and with movement of the handle 504. The position of the localization wire 506 relative to the introducer 502 may be adjusted. For example, the localization wire 506 position may be adjusted by the medical professional 501 by adjusting an insertion element 508. The insertion element 508 may be a button, toggle, scroll, pressure switch, sliding switch, or any other physical element coupled to the localization insertion device 500 usable to move the localization wire 506 relative to the introducer 502 or handle 504. For example, if the introducer 502 is removed from the patient in the pre-deployment state, the localization wire 506 is also removed from the patient. The localization wire 506 may be pre-positioned in an annulus of the introducer 502 and remains in a fixed position relative to the introducer 502 while in the pre-deployment state.

FIG. 5B depicts an example localization insertion device in a post-deployment state for subcutaneous insertion of a localization wire 506. In the post-deployment state shown in FIG. 5B, the localization wire 506 is coupled to the patient such that the localization wire 506 moves with movement of the patient, independent from movement of the localization insertion device 500. For example, if the introducer 502 is removed from the patient in the post-deployment state, at least a portion of the localization wire 506 may remain in the patient.

Deployment of the localization wire 506 may be caused by an adjustment of the insertion element 508. For example, adjustment of the insertion element 508 may cause a portion of the localization wire 506 to be exposed from an annulus of the introducer 502. For instance, adjustment of the insertion element 508 causes the localization wire to advance out of the introducer 502. A tip 510 and a shape memory portion 512 of the localization wire 506 may first be exposed as the localization wire 506 is deployed. The tip 510 and/or the shape memory portion 512 may cause the localization wire 506 to couple to the patient. In the example depicted, the shape memory portion 512 is a ring-shaped portion. Aspects of the shape memory portion 512 are further described at least in relation to FIG. 5C.

Deployment of the localization wire 506 may be reversable to enable the localization insertion device 500 to transition between the pre-deployment state of FIG. 5A and post-deployment state of FIG. 5B. Retraction of the localization wire 506 may be caused by an adjustment of the insertion element 508. The reversibility of deployment (e.g., by retracting the localization wire 506) may be limited. For example, the localization wire may not be retractable after a length of the localization wire exposed from the introducer exceeds a threshold length. In an instance, after a threshold percentage (e.g., 20-60%) of the shape memory portion 512 is exposed the localization wire 506 may no longer be retractable.

Figure 5C:
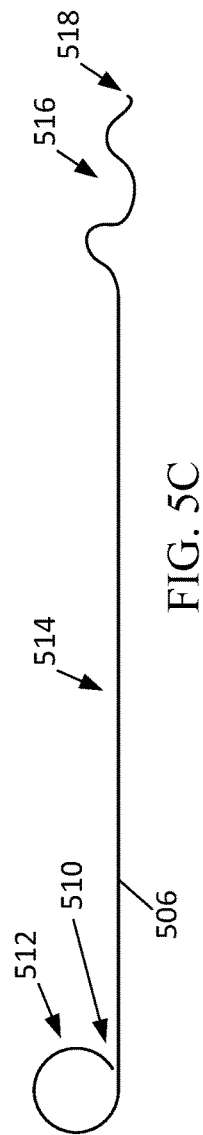
FIG. 5C depicts an example localization wire for subcutaneous insertion using the localization insertion device of FIG. 5A and FIG. 5B.
Figure 6A:
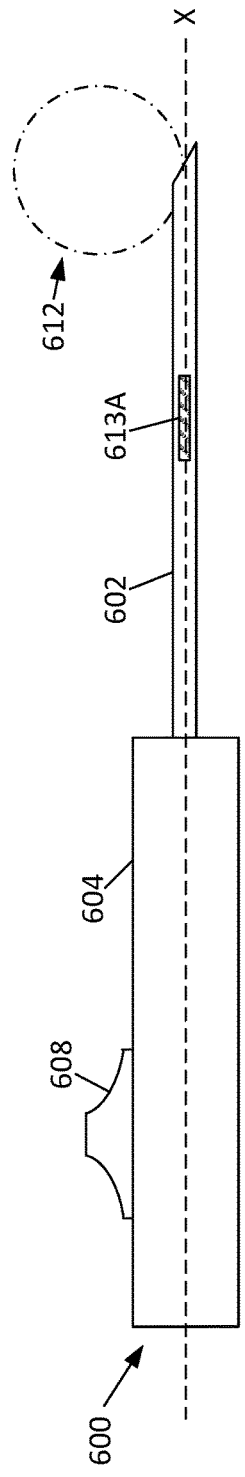
FIGS. 6A-D depict different perspectives of a localization insertion device with orientation marker(s).
Figure 6B:
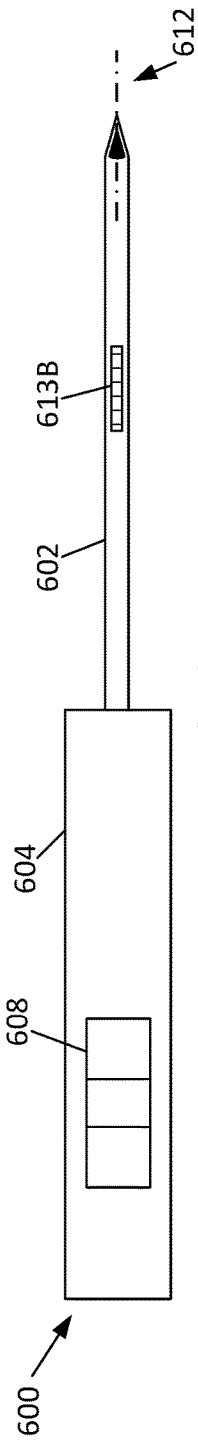
Figure 6C:
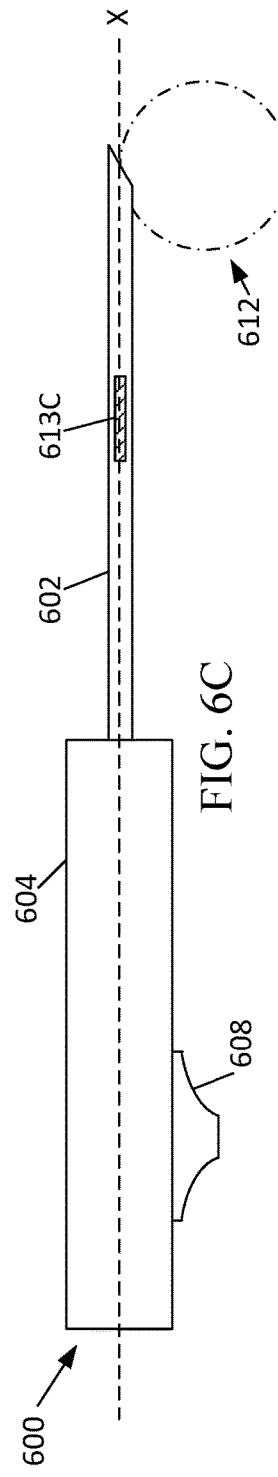
Figure 6D:
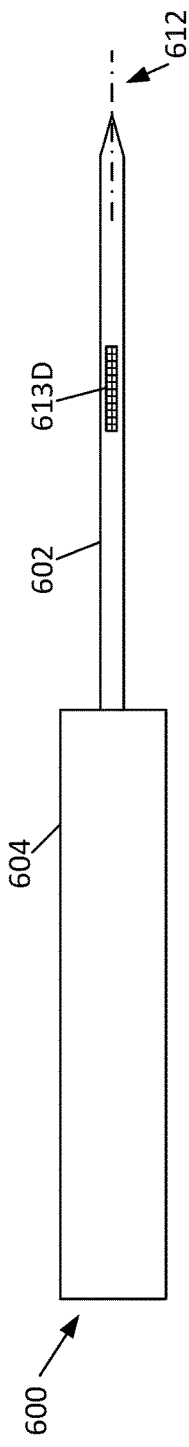

FIG. 5C depicts an example localization wire 506 for subcutaneous insertion using the localization insertion device 500 of FIG. 5A and FIG. 5B. As described herein, the localization wire 506 may be implanted in a patient with an introducer 502 such that the localization wire 506 remains in the patient when the introducer 502 is removed. The localization wire 506 includes a tip 510 to be implanted in the patient and an exterior end 518 extending outside the patient when the localization wire 506 is implanted. The localization wire 506 may include a plurality of portions. For example, the localization wire 506 may include a shape memory portion 512 adjacent to the tip 510 of the localization wire 506, a tail portion 516 adjacent to the exterior end 518, and an elongate portion 514 extending between the shape memory portion 512 and the tail portion 516.

When the localization wire 506 is deployed by the localization insertion device and implanted in the patient after removal of the introducer 502 from the patient, the shape memory portion 512 of the localization wire 506 may localize a lesion in the patient by taking on a shape that surrounds, encapsulates, points to, or otherwise indicates the location of the lesion in the patient. The shape memory portion 512 is made of a shape-memory material (e.g., alloy, polymer, etc.) capable of returning to an original shape after being deformed to a temporary shape. For example, the shape memory portion 512 may be a portion of the localization wire 506 that is under tension when inside the introducer 502. When the shape memory portion 512 is advanced into the patient, the tension of the shape memory portion 512 causes the shape memory portion 512 to curl from its linear position—similar to a spring.

In other examples, the shape memory material may be induced into the temporary shape (e.g., an elongate shape to be inserted into the introducer 502) using a variety of inducers such as temperature, light, chemical agent, magnetic field, mechanical force, etc. For example, the shape memory portion 512 may have an original shape (e.g., non-elongate shape) outside of the introducer, be straightened (a mechanical force) into a temporary shape (e.g., elongate shape) when inserted into an annulus of the introducer 502, and then return to the original shape when exiting the annulus of the introducer 502 when being deployed by the localization insertion device 500. Alternatively, the shape memory portion 512 may have an original shape (e.g., elongate shape) at a first temperature (e.g., a temperature lower than a body temperature of the patient) and may transition to the temporary shape (e.g., non-elongate shape) when reaching at least the body temperature of the patient (e.g., when the introducer is placed in the patient or when the shape memory portion 512 is deployed in the patient). In this instance, if the shape memory portion 512 reaches the inducing temperature prior to deployment, the mechanical forces exerted on the shape memory portion 512 by the annulus may hold the shape memory portion substantially in the original shape (e.g., elongate shape) until deployed by the introducer 502. Other inducers should be appreciated.

As shown, the non-elongate shape of the shape memory portion 512 may be a ring, such as an oval, circle, or oblong. Alternatively, the non-elongate shape of the shape memory portion 512 may be any two-dimensional shape such that, when the localization wire 506 is deployed by the introducer, the shape memory portion 512 extends in at least one direction outside of an introducer axis X defined by the introducer 502. The non-elongate shape of the shape memory portion 512 may cause the tip 510 of the localization wire 506 to intersect or approach the introducer axis X. For example, if the non-elongate shape of the shape memory portion 512 is a ring, the tip 510 may bend back towards the introducer axis X to form a ring that is substantially tangent to the introducer axis X. The shape memory portion 512 may come in a variety of sizes. For example, if the non-elongate shape is a ring in the shape of a circle, the diameter of the circle may be selectable (e.g., 1 cm, 1.5 cm, 2 cm, etc.).

When the localization wire 506 is implanted in the patient, the elongate portion 514 may be positioned inside the patient while the tail portion 516 protrudes from the patient. Because the tail portion 516 protrudes from the patient, the tail portion 516 may be malleable or flexible to be secured to an exterior of the patient with minimal protrusion. The elongate portion 514 and the tail portion 516 may be composed of different materials or may have different material characteristics. In an example, some portions of the localization wire 506 are braided. Additionally or alternatively, a segment within the elongate portion 514 and/or the tail portion 516 may have different characteristics from another segment along the same portion. For example, the elongate portion 514 may be stiff or inflexible relative to the tail portion 516, a first segment of the elongate portion 514 may be stiff or inflexible relative to a second segment of the elongate portion 514, or a first segment of the tail portion 516 may be stiff or inflexible relative to a second segment of the tail portion 516.

FIGS. 6A-D depict different perspectives of a localization insertion device 600 with orientation markers 613A-D on the introducer 602. As described herein, the orientation of the localization wire (e.g., localization wire 506 with a shape memory portion having a non-elongate shape of a ring) may be fixed relative to the orientation of the localization insertion device 600, the introducer 602, the handle 604, and/or the insertion element 608 (together, the "device components"), such that a predicted location of the ring 612 depends on the orientation one of the device components.

The orientation of one of the device components may be determined based on an orientation marker 613A-D. An orientation marker 613A-D may have echogenic properties to be viewable under and imager (e.g., ultrasound imaging) and may be positioned on the introducer 602 such that the orientation marker is visible when positioning the introducer 602 in a patient. The orientation marker 613A-D may be identified by a medical professional to manually determine an orientation of a device component or the localization wire or may be identified by an imager to automatically determine an orientation of one of the device components. The particular orientation marker 613A-D may also be automatically detected in an ultrasound image of the introducer 602. Based on the detection of an orientation marker 613A-D, the present technology is then able to provide guidance for a predicted location of the ring 612 as well as provide guidance to a medical professional on how to rotate the handle 604 to cause the ring 612 to be in plane with the ultrasound image.

In an example, multiple orientation markers 613A-D may be placed on the introducer 602 to indicate rotational orientation. For instance, a first orientation marker 613A shown in FIG. 6A indicates a predicted location of the ring 612 extending along the imaging plane defined by the ultrasound image in a positive y-axis direction (e.g., above the introducer axis X). A second orientation marker 613B shown in FIG. 6B indicates a predicted location of the ring 612 extending out of the imaging plane towards the imager (e.g. 90 degrees clockwise from the orientation defined by the first orientation marker 613A). A third orientation marker 613C shown in FIG. 6C indicates a predicted location of the ring 612 extending along the imaging plane in a negative y-axis direction (e.g., below the introducer axis X, 90 degrees clockwise from the orientation defined by the second orientation marker 613B, and 180 degrees from the orientation defined by the first orientation marker 613A). A fourth orientation marker 613D shown in FIG. 6D indicates a predicted location of the ring 612 extending out of the imaging plane away from the imager (e.g. 90 degrees clockwise from the orientation defined by the third orientation marker 613C, and 90 degrees counterclockwise from the orientation defined by the first orientation marker 613A, and 180 degrees from the orientation defined by the second orientation marker 613B). Alternatively, orientation of a device component or the localization wire may be determined based on a geometry of a device component (e.g., a tip of the introducer).

Figure 7A:
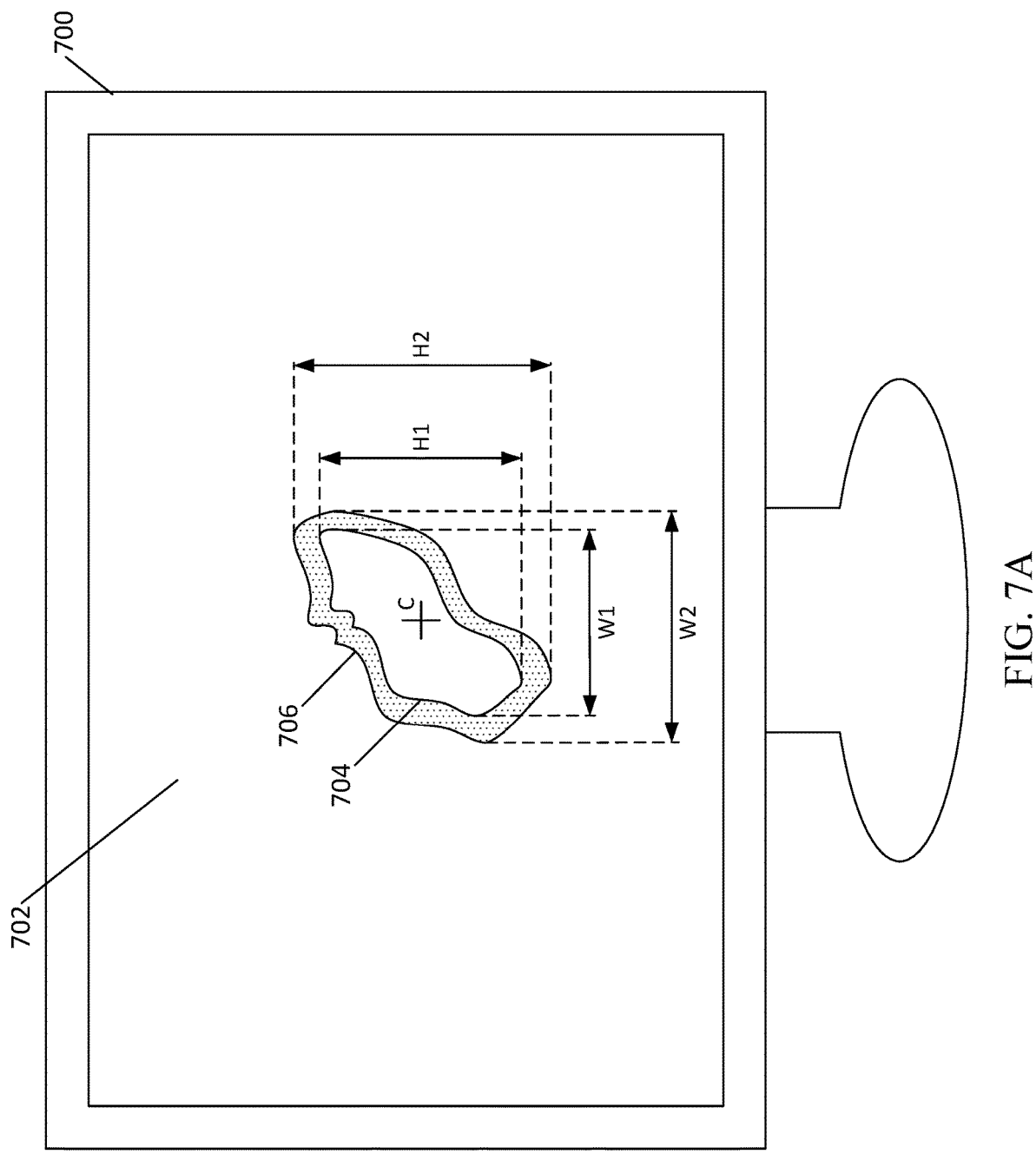
FIG. 7A depicts an example ultrasound image including a lesion.

FIG. 7A depicts an example display 700 showing an ultrasound image 702 including a lesion 704. The display 700 may share aspects described for the display 200 shown in FIG. 2 and the ultrasound image may share aspects described for the ultrasound image 201 shown in FIG. 2. The lesion 704 includes at least two dimensions along the imaging plane shown. For example, along the imaging plane, the lesion 704 has a lesion height H1 (which, as shown, is defined by the maximum distance between the edges of the lesion 704 in the y-direction), and a lesion width W1 (which, as shown, is defined by the maximum distance between the edges of the lesion 704 in the x-direction). Based on the lesion height H1 and the lesion width W1, a lesion center C may be defined as the center of the rectangle formed by the lesion height H1 and the lesion width W1 about the lesion 704. The edges of the lesion 704 used to determine the lesion height H1 and the lesion width W1 may be identified manually by a medical professional or automatically by the imaging technology. For instance, the borders of the lesion 704 may be automatically identified, or the borders of the lesion may be manually selected via inputs at the display 700. Additionally, the lesion center C may be identified manually or automatically.

A margin 706 may be selected or determined for the lesion 704 based on selected or pre-selected margin preferences. Margin dimensions may be generated manually or automatically based on the lesion dimensions. For example, a margin height H2 may be the lesion height H1 plus a height error and the margin width W2 may be the lesions width W1 plus a width error. Alternatively, the margin dimensions may be determined based on an input by the medical professional. The margin 706 may be displayed on the ultrasound image 702 concurrently with the lesion 704. In an example where the margin includes the same error from all edges of the lesion 704, the center of the margin is the same as the lesion center C.

Figure 7C:
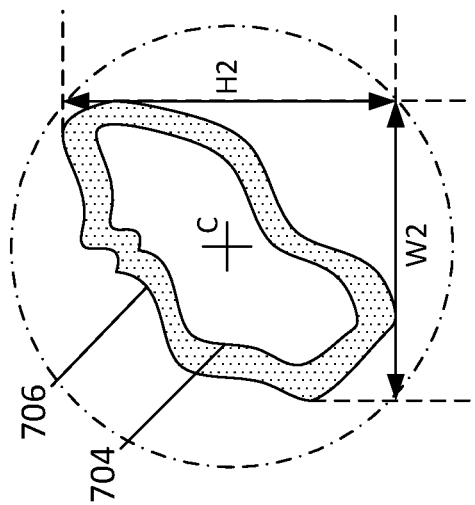
FIGS. 7B-C depict example ring sizes of a localization wire based on dimensions of the lesion and/or dimensions of the margin in FIG. 7A.
Figure 7B:
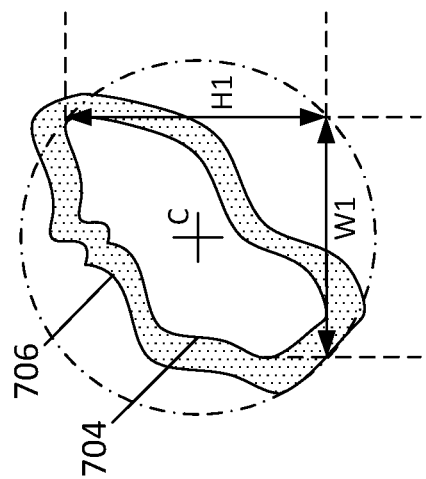

FIGS. 7B-C depict example ring sizes of a localization wire based on dimensions of the lesion 704 and/or dimensions of the margin 706 in FIG. 7A. A minimum ring dimension (e.g., minimum radius, minimum diameter, etc.) may be determined based on the lesion height H1, margin height H2, lesion width W1, margin width W2, and/or lesion center C. In the example shown in FIG. 7B, a minimum radius for a ring of a localization wire (e.g., shape memory portion 512 with a ring as a non-elongate shape) is determined based on the lesion height H1 and the lesion width W1. In the example shown in FIG. 7C, a minimum radius for a ring of a localization wire is determined based on the margin height H2 and the margin width W2. The minimum ring dimension determined for the lesion may be used to select a localization wire with a shape memory portion having at least the minimum ring dimension. In an example, selectable ring sizes may include 0.5 cm diameter (ring size A), 1 cm diameter (ring size B), and 1.25 cm diameter (ring size C). If the minimum ring dimension is a radius of 0.5 cm or less, then ring size A may be selected. If the minimum ring dimension is a radius greater than 0.5 cm and less than or equal to 1.0 cm, then ring size B may be selected. If the minimum ring dimension is a radius greater than 1.0 inch and less than or equal to 1.25 cm, then ring size C may be selected. The minimum ring dimension and/or suggested ring size may be displayed on the display 700. For instance, based on the lesion height H1 and lesion width W1 and desired or selected margins, the imaging system may automatically display the minimum ring dimension and/or suggested ring size.

Figure 7D:
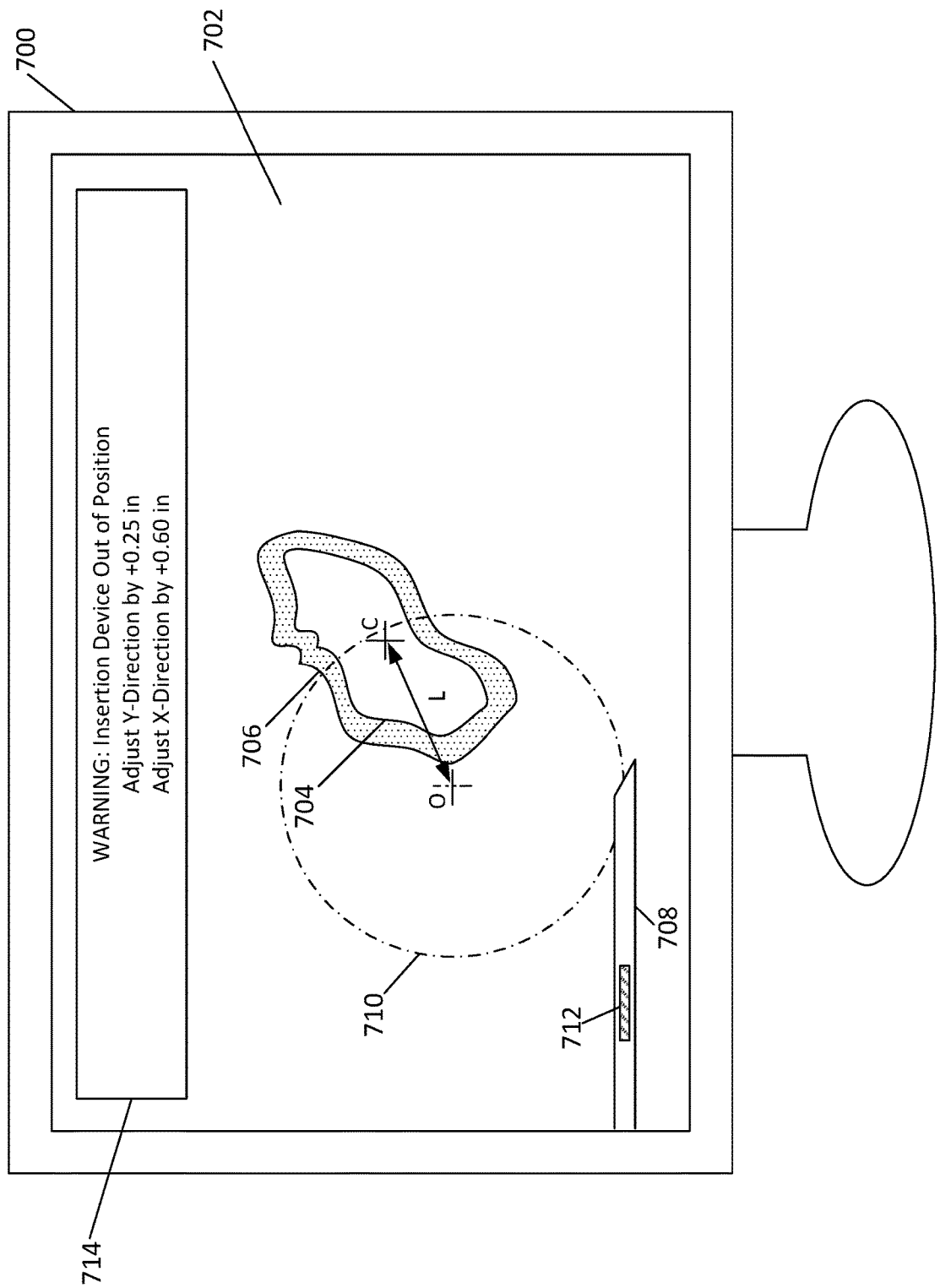
Figure 7F:
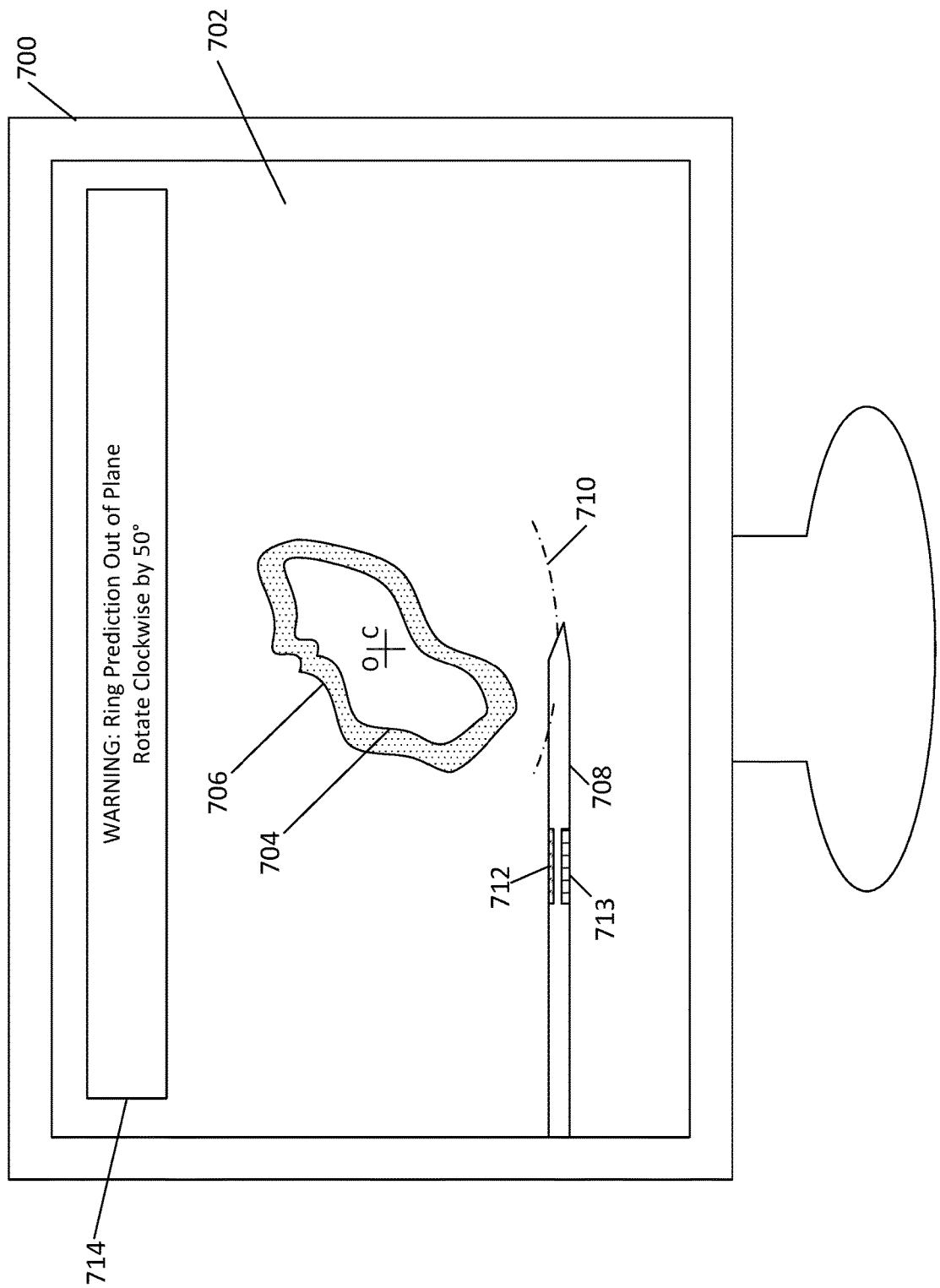
FIG. 7F depicts an example ultrasound image including the lesion and the introducer of FIGS. 7D-E where a portion of the predicted ring location lies outside of the imaging plane.

FIGS. 7D-E depict example ultrasound images including the lesion 704 of FIG. 7A, an introducer 708 (e.g., of a localization insertion device such as localization insertion devices 500, 600), and a predicted ring location indicator 710 of a localization wire, where the introducer 708 and the lesion 704 are both in the imaging plane of the ultrasound image 702. FIG. 7F depicts an ultrasound image 702 including the lesion 704 and the introducer 708 of FIGS. 7D-E where a portion of the predicted ring location indicator 710 lies outside of the imaging plane.

In FIG. 7D, the ultrasound image 702 is an image of the lesion 704 and of the introducer 708 after the introducer 708 has been inserted into the body of the patient and is in its pre-deployment state. The imaging system may automatically identify the introducer based on its physical characteristics, such as is linear shape and echogenic properties. Upon identifying the introducer 708, the imaging system may display a predicted ring location indicator 710. The predicted ring location indicator 710 indicates the predicted position of the ring portion of the localization wire. The predicted ring location indicator 710 is based on the position and orientation of the introducer 708. The rotational orientation of the introducer may be determined by identifying a tip shape of the introducer and/or detecting an orientation marker 712. The predicted ring location indicator 710 is also based on the properties of the selected ring (e.g., a ring diameter or ring radius, a ring center, a ring gauge, a ring material composition, a ring tip geometry, and a ring extension property). Further, the predicted ring location indicator 710 may be based on tissue properties near the tip of the introducer 708 and along the path that the localization wire will travel when deployed. Because the ring of the localization wire may travel in two dimensions, unlike the linear biopsy needle discussed above, the tissue composition may cause additional deflection and have different effects on deflection. For example, the entire ring may deflect or a portion of the ring may deflect to warp the shape of the ring. A deflection probability indicator may also be displayed to indicate the likelihood or confidence that the localization wire will follow the path of the predicted ring location indicator 710. The deflection probability indicator 710 may have the same or similar features (e.g., heat map, colors, etc.) and the deflection probability indicator discussed above with respect to the biopsy needle. A medical professional may utilize the predicted ring location indicator 710 as a guide when placing the localization wire.

The ring size may be manually or automatically selected. The selection of the ring size may be based on the minimum ring dimension described above. An indication of the ring size may be displayed on the display 700 along with the predicted ring location indicator 710. A plurality of predicted ring location indicators 710 may be displayed if the ring size is unknown, interchangeable, or variable. If a portion of the predicted ring location is outside of imaging plane, then that portion of the predicted ring location indicator 710 may not be shown on the display 700 (e.g., as shown in FIG. 7F). Based on the ring size and the position of the introducer 708, an in-plane predicted ring center O may be generated. The in-plane predicted ring center O may be shown on the display 700 regardless of whether the predicted ring location indicator 710 is in the imaging plane of the ultrasound image 702 (e.g., as shown in FIG. 7F).

The three-dimensional position of the introducer may be evaluated. The depth of the introducer 708, or determination of plane diversion of the introducer 708 outside of the imaging plane, may be evaluated using techniques described at least with respect to FIG. 4.

Additional guidance may also be provided to the medical professional based on the predicted ring location indicator 710. The position of the introducer 708 may be proper for deployment of the ring if, assuming the ring is rotationally oriented in-plane with the imaging plane, the predicted ring location indicator 710 includes the lesion 704 and at least a desired margin 706 about the lesion 704. As otherwise referred to herein, a proper position, a permissible position, and a deployment position, indicate that the introducer 708 is in an acceptable or desirable position to deploy the ring. An evaluation of proper positioning of the introducer 708 may be determined based on if the in-plane predicted ring center O is within a threshold distance of the lesion center C. For instance, as shown in FIG. 7D, the in-plane predicted ring center O is a centering distance L away from the lesion center C. The centering distance L may be automatically calculated based on the locations of the in-plane predicted ring center O and the lesion center C. As described herein, the in-plane predicted ring center O, may be determined based on ring properties (e.g., a ring diameter or ring radius, a ring center, a ring gauge, a ring material composition, a ring tip geometry, and a ring extension property). The lesion center C may be based on features of the lesion 704 (e.g., lesion height H1, lesion width W1, lesion area, lesion shape, etc.) and/or features of the margin (e.g., margin height H2, margin width W2, margin shape, etc.), and may be determined automatically or based on input by a medical professional.

After identifying the lesion center C and the in-plane predicted ring center O, the centering distance L may be calculated. The centering distance L may be compared to a threshold distance. The threshold distance may be based on ring properties, features of the lesion, features of the margin, and/or a predicted deflection. Based on the comparison of the centering distance L and the threshold distance, a notification may issue. For example, if the centering distance L is less than or equal to the threshold distance, then a notification may issue indicating that the position of the introducer 708 is proper. If the centering distance L is greater than the threshold distance, then a notification may issue indicating that the position of the introducer 708 is improper.

As an alternative to calculating a centering distance L, the coordinate position of the in-plane predicted ring center O may be evaluated based on a threshold area about the lesion center C. The threshold area may be a circle centered about the lesion center C having a threshold radius. Alternatively, the threshold area may be non-symmetric about the lesion center C. For example, the threshold area may be a proportion of the dimensions of the lesion. The coordinate position of the in-plane predicted ring center O may be compared with the threshold area to determine if the coordinate position lies inside or outside of the threshold area. Similar to the comparison of distances above, based on the comparison of the coordinate position of the in-plane ring center O and the threshold area, a notification may issue indicating if the position of the introducer 708 is proper or improper.

As an alternative to evaluating the position of the introducer 708 based on shape centers (i.e., the in-plane predicted ring center O and the lesion center C), the predicted ring location indicator 710 may be compared with identified edges or boundaries of the lesion 704 and/or margin 706. Similar to the comparison of distances and coordinate positions above, based on the comparison of the predicted ring location indicator 710 and the lesion 704 and/or margin 706, a notification may issue indicating if the position of the introducer 708 is proper or improper. For instance, as shown in FIG. 7D, the predicted ring location indicator 710 would not encompass the lesion 704. Thus, the medical professional would not want to deploy the localization ring with the introducer 708 in its present position. In contrast, in FIG. 7E, the predicted ring location indicator 710 is positioned in the proper location such that it encompasses the lesion 704.

Proper positioning of the introducer 708 may be indicated on the display 700 (e.g., color change, text, shading, or other indicator of correct two-dimensional and/or three-dimensional positioning). As an example, the predicted ring location indicator 710 may change color when the introducer 708 is properly positioned. For instance, when the introducer is not properly positioned, the predicted ring location indicator 710 may be a first color and when the introducer 708 is properly positioned, the predicated ring location indicator 710 may be a second color. The color of the predicted ring location indicator 710 may also gradually change as the introducer 708 moves towards the proper position. Additionally or alternatively to color, the line type or line properties of the predicted ring location indicator 710 may change based on proper positioning of the introducer 708. If the introducer 708 is not positioned for proper deployment, an alert 714 may be shown on the display 700 indicating that the introducer 708 is out of position (e.g., the alert 714 shown in FIG. 7D). The alert 714 may also provide a suggested amount of movement of the introducer 708 for proper positioning (e.g., movement in the y-direction and/or movement in the x-direction along the imaging plane shown in the ultrasound image 702). The suggested movement may be based on comparison of the location of the lesion center C to the location of the in-place predicted ring center C.

In addition to the two-dimensional and/or three-dimensional position of the introducer 708, the rotational orientation of the introducer 708 may be evaluated. The rotational orientation of the introducer 708 and/or predicted ring location indicator 710 may be based on an orientation marker 712 visible in the ultrasound image 702, as further described at least with respect to FIGS. 6A-D. For example, the first orientation marker 712 shown in FIGS. 7D-E indicates the predicted ring location indicator 710 is in-plane with the ultrasound image 702, while the second orientation marker 713 shown in FIG. 7F indicates that a portion of the predicted ring location indicator 710 lies outside of the imaging plane. Thus, rotational orientation of the predicted ring location indicator 710 may be determined manually or automatically by identifying the visible orientation marker(s). If a portion of the predicted ring location indicator 710 lies substantially outside of the imaging plane, then an alert 714 may be shown on the display indicating that the ring is predicted to be out of plane (e.g., the alert 714 shown in FIG. 7F). The alert 714 may also provide a suggested degree of rotation of the introducer 708 in either a clockwise and/or counterclockwise direction. The suggested degree of rotation may be based on the orientation identified (e.g., based on orientation marker(s)). If the rotational orientation of the introducer 708 is proper for deployment, then an indication of proper positioning may be shown on the display 700 (e.g., color change, text, shading, or other indicator of correct three-dimensional positioning). Thus, when the introducer 708 is in a deployment position (e.g., in-plane predicted ring center O and the lesion center C are close enough and the predicted ring location indicator 710 is in plane, or the predicted ring location indicator 710 encases the lesion 704 and/or the margin 706, or as otherwise described herein), an indication may be shown on the display 700.

Figure 8:
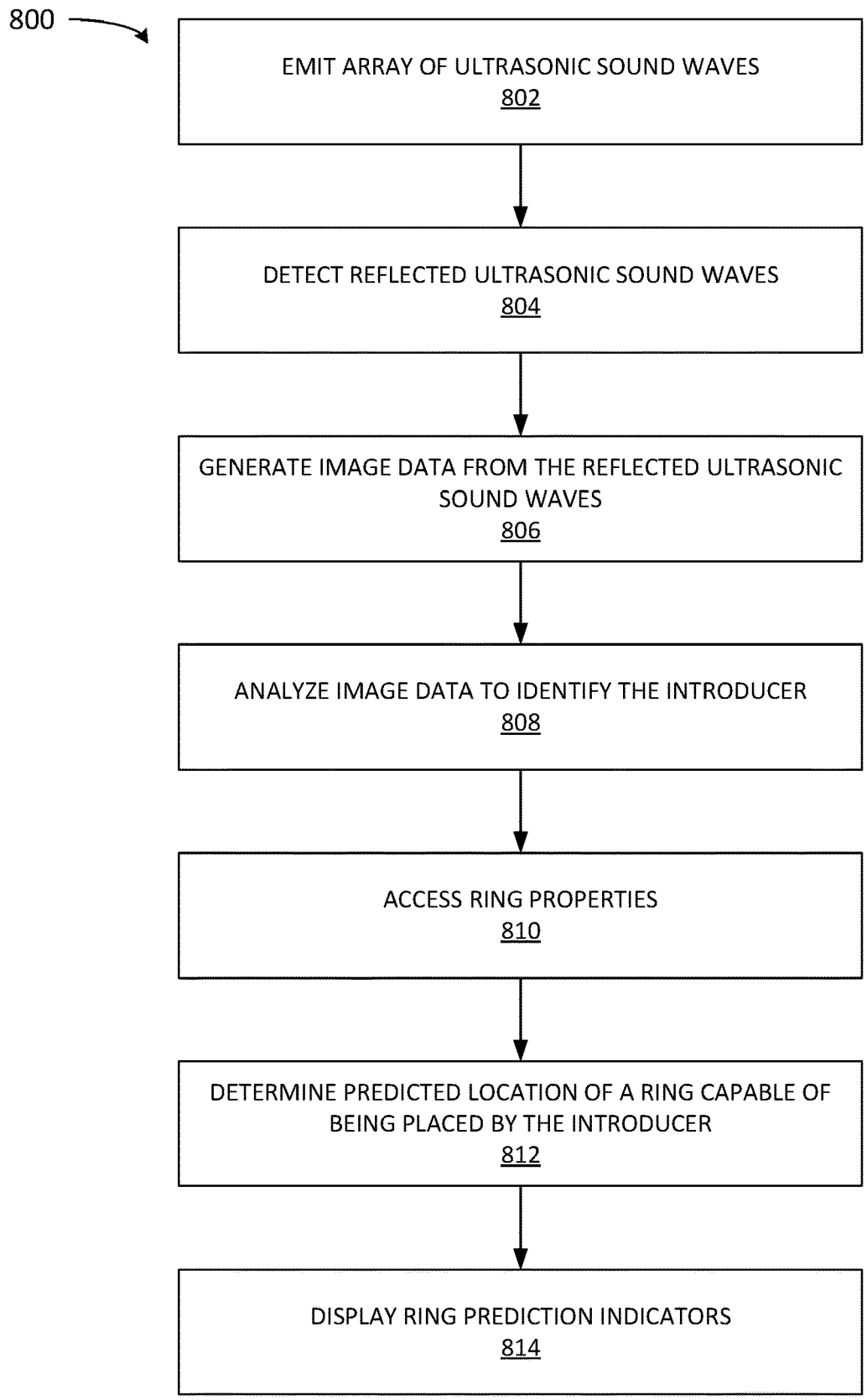
FIG. 8 depicts an example method for visualization of a localization wire.

FIG. 8 depicts an example method 800 for visualization of a localization wire. The predictive visualization method 800 provides for additional guidance and introducer prediction indicators to be displayed on an ultrasound image as a localization procedure is being performed. As such, a surgeon or other medical professional performing the localization procedure may receive substantially real-time guidance for performing the localization procedure. The operations of method 800 and the other methods discussed herein may be performed by at least one processor in conjunction with other components of a suitable operating environment, such as the operating environment 150 in FIG. 1G, within a system such as system 100 depicted in FIGS. 1A-1C.

Operations 802-808 of the visualization method 800 may be similar to that of operations 302-308 of method 300A in FIG. 3A, except for the visualization method 800 is applied to an introducer capable of placing a localization wire including a two-dimensional shape portion (e.g., shape memory portion 512 of localization wire 506 in FIG. 5C, which may be a ring).

At operation 810, properties for the ring and/or the introducer are accessed or otherwise determined. The properties for the ring include at least one of a ring diameter, ring radius, ring center, ring gauge, ring material composition, ring tip geometry, and a ring extension property, among other potential localization wire properties. The properties for the ring may be accessed by querying a database stored locally in the visualization system 100 or a remote database accessible from the visualization system 100. In an example, a user interface may first be displayed at the beginning of a localization procedure to allow for a selection or input a type or size of ring or localization wire to be used in the localization procedure (e.g., as may be associated with a ring dimension). In an example, the input into the user interface may indicate a particular make or model of the ring or localization wire. In such an example, the input into the user interface may be used to query the respective database to access or determine the properties for the ring or localization wire indicated by the input into the user interface. In other examples, the properties of the ring or localization wire (e.g., ring diameter or radius, shape memory material strength, ring gauge, wire gauge, wire length, etc.) are provided directly as input into the user interface. In such an example, no database query is performed as the properties have already been provided directly.

At operation 812, the predicted location of the ring is determined. Determining the predicted location of the ring may include determining the two-dimensional, three-dimensional position, and/or rotational orientation of the introducer in the pre-deployment position and/or the properties of the ring. For example, a predicted location of the ring post-deployment may be determined. In such an example, various aspects of the ring, such as the ring tip, ring diameter or radius, etc., may be determined for the ring in the post-deployment state. The determination of the predicted location of the ring may be based on the ring properties accessed or determined in operation 810. In addition, the determined predicted location for the ring may also be based on tissue properties.

At operation 814, one or more ring prediction indicators are displayed on an ultrasound image. For example, the ring prediction indicators may include one or more of a predicted ring location existing in the imaging plane of the ultrasound image (e.g., predicted ring location indicator 710), a predicted ring center (e.g., predicted ring center O), a deflection probability indicator, a position alert, or an orientation alert. Displaying the prediction indicators may also include changing the state of the prediction indicators. For instance, as the introducer in its pre-deployment state is moved within the patient, the state of the prediction indicators may change. As an example, the displayed predicted ring location may change as the introducer is repositioned and/or rotationally re-oriented. The prediction indicators may also include audible indicators or tactile indicators in the localization insertion device.

The display of the ring prediction indicators may be activated when certain conditions are met and/or the display of the ring prediction indicators may be toggleable. As an example, the imaging system may identify when the localization wire is beginning to be deployed from the introducer. That event may be detected by a highly echogenic element beginning to protrude from the tip of the introducer in the ultrasound image. Upon detection of such an event, the display of the ring prediction indicators may be activated. Accordingly, a medical professional may activate the display of the ring prediction indicators by beginning the deployment process (e.g., moving the button on the handle of a localization device forward). If the ring prediction indicators indicate that the introducer is the incorrect position, the medical professional may retract the localization wire and reposition in the introducer. In some examples, retraction of the localization wire back into the introducer may cause the display of the ring prediction indicators to cease. In other examples, the display of the ring prediction indicators may persist after retraction of the localization wire. The display of the ring prediction indicators may also be toggleable. For instance, an input may be received that turns on or off the display of one or more the ring prediction indicators.

In addition to the ring prediction indicators, additional positioning indicators may be displayed indicating to the medical professional how to alter the position of the introducer to more accurately target the lesion or area of interest. For instance, the lesion or area of interest may be identified through image analysis and/or user input. If the predicted ring location is not aligned to properly localize the lesion post-deployment, positioning indicators may be displayed to guide the medical professional on how to move the introducer into a position where the predicted ring location accurately targets the lesion. Such positioning indicators may be in the form of arrows and/or text, among other indicators, that provide the positioning guidance. In addition, visual, tactile, and/or audible positioning indicators may be displayed that indicate proper positioning of the introducer. As an example, when the introducer is positioned such that the predicted ring location will properly target the lesion, tactile, audible, and/or visual feedback may be provided. For instance, an audible sound may be provided, and the sound may change volume or frequency as the introducer is moved toward or away from properly targeting the lesion or area of interest.

Additional visualization techniques described above with respect to a biopsy needle and a biopsy procedure may be applied to an introducer capable of placing a localization wire. For example, determining a deflection probability of the predicted ring location of a localization wire post-deployment may be similar to determining a deflection probability described in method 300B in FIG. 3B. For example, ring properties and tissue properties along the path of the predicted ring location may be evaluated and used to generate a probability indicator. Additionally or alternatively, evaluating if the introducer and/or predicted ring location are experiencing plane diversion may be similar to the techniques described in method 400 of FIG. 4.

Figure 9:
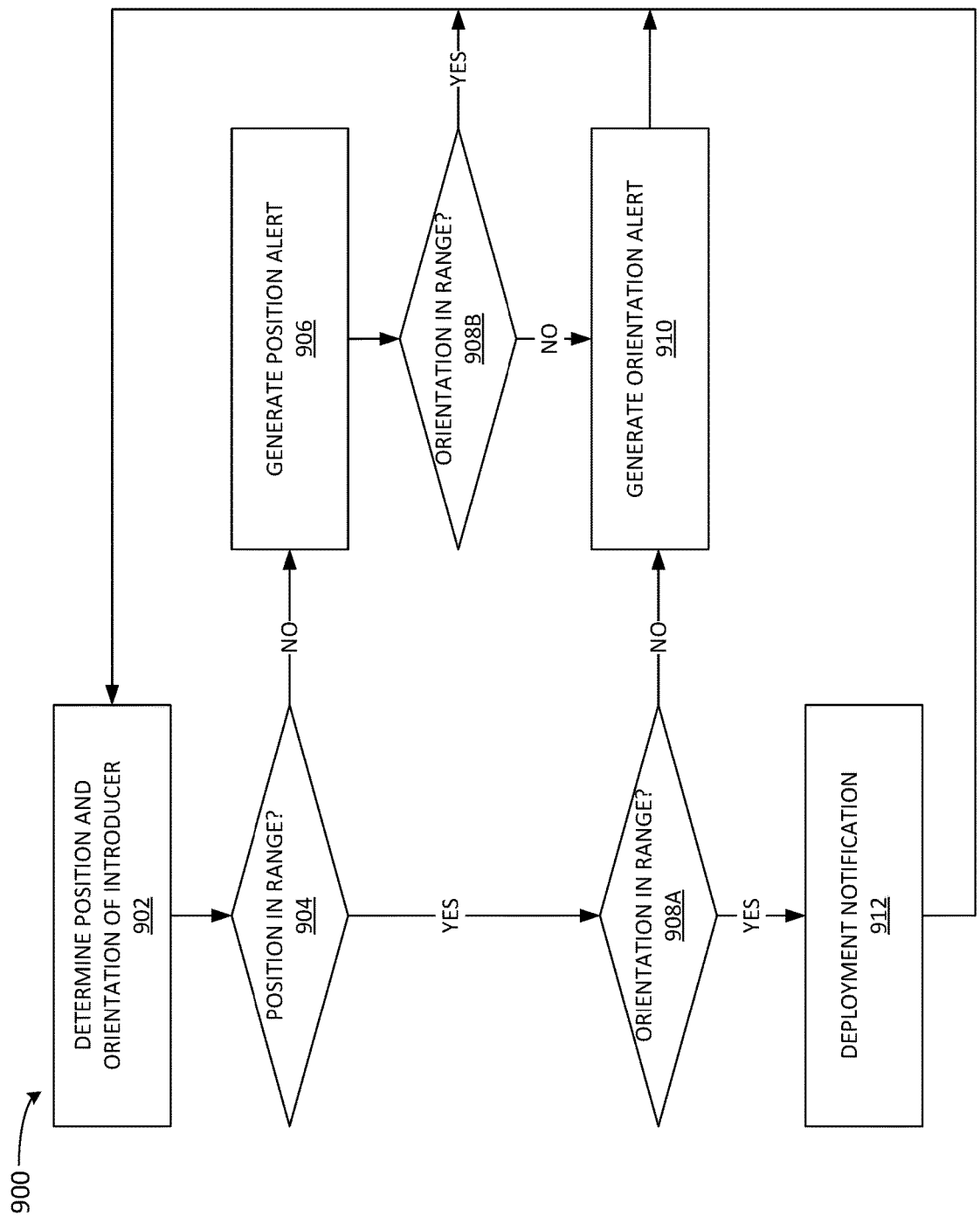
FIG. 9 depicts an example method for detecting position and orientation information of an introducer along an imaging plane.

FIG. 9 depicts an example method 900 for detecting position and orientation information of an introducer and/or predicted ring location along an imaging plane. At operation 902, a position and orientation of an introducer are determined. The position information includes two-dimensional and/or three-dimensional information relating to the position of the introducer, such as depth information and plane diversion information, and x-y coordinate information and deflection information along the plane. The orientation information includes information about the rotational orientation of the introducer and/or predicted ring location, such as a rotation angle and rotation direction relative to the imaging plane. Position information and orientation information may be determined using the techniques described herein.

At determination 904, the position is evaluated. As further described herein, the position of the introducer may be permissible for deployment of a ring of a localization wire when the predicted ring location encompasses the lesion plus a desired margin or when a predicted center of the ring aligns with, or is within a desired radius of, of the center of the lesion (assuming that the ring deploys in the imaging plane). If the position is determined to be improper for deployment of the ring (e.g., the predicted ring location does not include the entire lesion or the predicted center of the ring is not close enough to the lesion center), then a position alert is generated at operation 906. The position alert may include visual, tactile, and/or audible indicators, as further described above. In an example, the position alert may also include direction indicators (e.g., distance in y-direction and distance is x-direction) to assist a medical profession in moving the introducer until positioning is permissible.

If, however, the position of the introducer is permissible for deployment of the ring, then the orientation of the introducer is evaluated at determination 908A. Rotational orientation of the introducer may be permissible when the introducer and/or predicted ring location are in-plane, or substantially in plane (e.g., within acceptable degrees of rotation), with the imaging plane. If the orientation is determined to be impermissible for deployment of the ring (e.g., the introducer and/or predicted ring location are substantially out of plane), then an orientation alert is generated at operation 910. The orientation alert may include visual, tactile, and/or audible indicators, as further described above. In an example, the orientation alert may also include direction indicators (e.g., rotation angle and rotation direction) to assist a medical profession in rotating the introducer until the orientation is permissible.

At determination 908B, the orientation is evaluated using the same techniques as determination 908A. Thus, if the orientation is determined to be improper at determination 908A or at determination 908B, then an orientation alert is generated at operation 910. Determinations 908A and 908B diverge, however, if the orientation is evaluated as permissible for deployment of the localization wire. At determination 908A, the position of the introducer was determined to be proper at determination 904, thus, if both the position and orientation are permissible (e.g., flowing "YES" at determinations 904 and 908A), then a notification may be issued at operation 912 indicating that the introducer and predicted ring location are permissible to deploy the localization wire at the evaluated position and orientation. Alternatively, at determination 908B, the position of the introducer was determined to be impermissible at determination 904 and thus, regardless of orientation, the introducer is not positioned for deployment. If the orientation is permissible, an additional alert (in addition to the position alert at operation 906) may not be issued.

Although the method 900 describes evaluation of position (e.g., at determination 904) prior to evaluation of orientation (e.g., at determinations 908A, 908B), position and orientation may be evaluated in any order or concurrently. Operations 902-912 may repeat as required or desired. For example, operations 902-912 may repeat when the position and/or orientation of the introducer and predicted ring location change, as may be detected using techniques described herein.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

Further, as used herein and in the claims, the phrase "at least one of element A, element B, or element C" is intended to convey any of: element A, element B, element C, elements A and B, elements A and C, elements B and C, and elements A, B, and C. In addition, one having skill in the art will understand the degree to which terms such as "about" or "substantially" convey in light of the measurement techniques utilized herein. To the extent such terms may not be clearly defined or understood by one having skill in the art, the term "about" shall mean plus or minus ten percent.

What is claimed is:

1. A method for providing guidance for an introducer, the method comprising:
    emitting an array of ultrasonic sound waves from an ultrasonic transducer of an ultrasound probe;
    detecting reflected ultrasonic sound waves by the ultrasonic transducer, wherein the reflected ultrasonic sound waves include at least a portion of the array of ultrasonic sound waves after being reflected from an interior of a patient;
    generating image data from the reflected ultrasonic sound waves;
    identifying, by a processor, within the generated image data, at least a portion of the introducer within the interior of the patient, wherein the introducer is elongated along an introducer axis that is in plane with an imaging plane of the ultrasound probe, and the identification of the introducer includes a rotational orientation of at least the portion of the introducer around the introducer axis;
    based at least in part on the identification of at least the portion of the introducer, determining, by the processor, a predicted location of a ring of a localization wire coming out of the introducer, the localization wire comprising a shape memory portion and a tail portion, the shape memory portion being configured to take on a shape that encapsulates a location of a lesion in the patient;
    displaying, on a display operatively connected to the processor, an ultrasound image based on the generated image data;
    displaying, on the ultrasound image, at least one indicator for the predicted location of the ring; and
    determining a deflection probability for the predicted location of the ring based on at least one of: (1) experimental data for a type of ring and (2) one or more stored properties of the ring.

2. The method of claim 1, wherein the ring is a portion of the localization wire having shape memory characteristics.

3. The method of claim 1 wherein displaying the at least one indicator for the predicted location of the ring includes displaying at least one of an in-plane predicted ring center of the ring or the predicted ring location of the ring.

4. The method of claim 1, wherein identifying at least the portion of the introducer comprises determining the rotational orientation of at least the portion of the introducer based on an orientation marker disposed on the introducer and included within the generated image data, and wherein an orientation of the ring is based on the orientation of the introducer.

5. The method of claim 1, wherein the one or more stored properties of the ring comprise at least one of a ring diameter, a gauge of the ring, a ring material composition, a ring tip geometry, and a ring extension property.

6. The method of claim 5, wherein the one or more stored properties of the ring are based on user input regarding a size of the ring.

7. The method of claim 5, wherein determining the deflection probability is further based on tissue properties of the interior of the patient along a ring trajectory for the ring.

8. The method of claim 5, further comprising displaying a deflection probability indicator on the ultrasound image, wherein the deflection probability indicator indicates a range for a ring location based on the determined deflection probability.

9. The method of claim 8, wherein the deflection probability indicator indicates a range of probabilities for the predicted ring location.

10. The method of claim 1, further comprising: determining that a portion of the predicted ring location is outside the imaging plane of the ultrasound probe; and in response to determining that the portion of the predicted ring location is outside of the imaging plane of the ultrasound probe, displaying an orientation alert.

11. The method of claim 10, wherein the orientation alert includes displaying a recommended correction angle to rotate the introducer.

12. The method of claim 1, further comprising:
    determining that the introducer is not in a deployment position; and
    in response to determining that the introducer is not in the deployment position, displaying a position alert.

13. The method of claim 12, wherein determining that the introducer is not in the deployment position includes one of:
    comparing an in-plane predicted ring center with a lesion center; or
    comparing the predicted location of the ring with a boundary of a lesion.

14. The method of claim 12, wherein the position alert includes displaying a recommended correction distance to move the introducer.

15. The method of claim 1, the method further comprising determining that the introducer has diverted out of the imaging plane of the ultrasound probe, including:

determining a first apparent depth for the introducer at a first time;
determining a second apparent depth for the introducer at a second time subsequent to the first time, the second apparent depth being greater than the first apparent depth;
determining a third apparent depth for the introducer at a third time subsequent to the second time, the third apparent depth being less than the second apparent depth; and
based on the third apparent depth being less than the second apparent depth and the second apparent depth being greater than the first apparent depth, determining that the introducer has diverted out of the imaging plane of the ultrasound probe.

16. The method of claim 1, wherein the predicted location of the ring is along a direction that has a different orientation from the introducer axis of the introducer.

17. A system comprising:
an ultrasound probe comprising an ultrasonic transducer, the ultrasonic transducer configured to emit an array of ultrasonic sound waves and detect reflected ultrasonic sound waves, wherein the reflected ultrasonic sound waves include at least a portion of the array of ultrasonic sound waves after being reflected within an interior of a patient;
a display;
at least one processor operatively connected to the display and the ultrasound probe; and
memory, operatively connected to the at least one processor, storing instructions that when executed by the at least one processor perform a set of operations comprising:
generating image data from the reflected ultrasonic sound waves;
identifying, by the at least one processor, within the generated image data, an introducer within the interior of the patient, wherein the introducer is elongated along an introducer axis that is in plane with an imaging plane of the ultrasound probe, and the identification of the introducer includes a rotational orientation of the introducer around the introducer axis;
based at least in part on the identification of the introducer, determining, by the at least one processor, a predicted location of a ring of a localization wire coming out of the introducer based on one or more stored properties of the ring, the localization wire comprising a shape memory portion configured to take on a shape that encapsulates a location of a lesion in the patient;
displaying, on a display operatively connected to the at least one processor, an ultrasound image based on the generated image data;
displaying, on the ultrasound image, at least one indicator for the predicted location of the ring; and
determining a deflection probability for the predicted location of the ring based on at least one of: (1) experimental data for a type of ring and (2) the one or more stored properties of the ring.

18. The system of claim 17, wherein the predicted ring location is along a direction that has a different orientation from the introducer axis of the introducer.

19. The system of claim 17, wherein the introducer includes a plurality of orientation markers, each orientation marker of the plurality of orientation markers having a distinct echogenic property visible under ultrasound imaging, and wherein each orientation marker of the plurality of orientation markers is circumferentially spaced around the introducer axis to indicate rotational orientation of the introducer under ultrasound imaging.

20. A method for providing guidance for placement of a localization wire with an introducer, the method comprising:
displaying a user interface for selecting a ring to be used for a localization procedure, wherein the ring is a portion of a localization wire capable of being placed by an introducer;
receiving a selection of the ring at the user interface, the selected ring to be used for the localization procedure;
determining one or more ring properties for the selected ring, wherein the ring properties include at least one of a ring diameter, a ring gauge, a ring material composition, a ring tip geometry, or a ring extension property;
emitting an array of ultrasonic sound waves from an ultrasonic transducer of an ultrasound probe;
detecting reflected ultrasonic sound waves by the ultrasonic transducer, wherein the reflected ultrasonic sound waves include at least a portion of the array of ultrasonic sound waves after being reflected from an interior of a patient;
generating an ultrasound image from the reflected ultrasonic sound waves;
identifying the introducer within the generated ultrasound image, wherein the introducer is elongated along an introducer axis that is in plane with an imaging plane of the ultrasound image;
determining a position and an orientation of the introducer, wherein the orientation of the introducer includes a rotational orientation of the introducer around the introducer axis;
based on the position and orientation of the introducer and the one or more determined ring properties, determining a predicted ring location of the selected ring coming out of the introducer, the ring comprising a shape memory portion configured to take on a shape that encapsulates a location of a lesion in the patient;
based on the predicted ring location, displaying a predicted ring location indicator; and
determining a deflection probability for the predicted ring location based on at least one of: (1) experimental data for a type of ring and (2) the one or more determined ring properties.

21. The method of claim 20, the method further comprising displaying a position notification and orientation notification for the introducer, wherein the position notification includes displaying a recommended correction distance in a direction to move the introducer and wherein the orientation notification includes displaying a recommended correction angle to rotate the introducer.

22. The method of claim 20, the method further comprising:
based on the position and orientation of the introducer and the determined ring properties, estimating a predicted ring center of the selected ring;
identifying a lesion within the generated ultrasound image, the lesion having a boundary and a center; and
determining that the introducer is in a deployment position based on one or more of:
the predicted ring location and the boundary of the lesion; or
the predicted ring center and the center of the lesion.

23. The method of claim 20, wherein determining the orientation of the introducer includes:

identifying an orientation marker disposed on the introducer within the generated ultrasound image.

24. The method of claim 20, wherein the predicted location of the ring of the localization wire is along a direction that has a different orientation from a longitudinal the introducer axis of the introducer.

\* \* \* \* \*